(12) United States Patent
Johnson et al.

(10) Patent No.: US 8,366,617 B2
(45) Date of Patent: Feb. 5, 2013

(54) BREAST SCANNING SYSTEM

(75) Inventors: Steven A. Johnson, Salt Lake City, UT (US); Michael J. Berggren, Salt Lake City, UT (US); David T. Borup, Salt Lake City, UT (US); Barry K. Hanover, Salt Lake City, UT (US); James W. Wiskin, Salt Lake City, UT (US); Jeff Pattee, Salt Lake City, UT (US)

(73) Assignee: CVUS Clinical Trials, LLC, Salt Lake City, UT (US)

( * ) Notice: Subject to any disclaimer, the term of this patent is extended or adjusted under 35 U.S.C. 154(b) by 1283 days.

(21) Appl. No.: 12/152,631

(22) Filed: May 14, 2008

(65) Prior Publication Data

US 2008/0319318 A1    Dec. 25, 2008

Related U.S. Application Data

(60) Provisional application No. 60/930,377, filed on May 15, 2007, provisional application No. 60/930,413, filed on May 15, 2007.

(51) Int. Cl.
*A61B 8/00* (2006.01)

(52) U.S. Cl. ........................................ 600/437; 600/459

(58) Field of Classification Search ........... 600/437–469
See application file for complete search history.

(56) References Cited

U.S. PATENT DOCUMENTS

| 3,765,403 | A | 10/1973 | Brenden |
|---|---|---|---|
| 3,805,596 | A | 4/1974 | Klahr |
| 3,885,224 | A | 5/1975 | Klahr |
| 3,963,933 | A | 6/1976 | Henkes |
| 4,047,520 | A | 9/1977 | Soldner et al. |
| 4,074,564 | A | 2/1978 | Andersen |
| 4,075,883 | A | 2/1978 | Glover |
| 4,100,916 | A | 7/1978 | King |
| 4,105,018 | A | 8/1978 | Greenleaf et al. |
| 4,109,642 | A | 8/1978 | Reid et al. |
| 4,109,644 | A | 8/1978 | Kojima |
| 4,112,941 | A | 9/1978 | Larimore |
| 4,120,291 | A | 10/1978 | Paton et al. |
| 4,222,274 | A | 9/1980 | Johnson |
| 4,252,125 | A | 2/1981 | Linuma |
| 4,282,880 | A | 8/1981 | Gardineer et al. |
| 4,298,009 | A | 11/1981 | Mezrich et al. |

(Continued)

FOREIGN PATENT DOCUMENTS

| DE | 19709224 | 9/1998 |
|---|---|---|
| EP | 0105812 | 3/1986 |

(Continued)

OTHER PUBLICATIONS

U.S. Appl. No. 12/152,637, filed May 14, 2008; Steven A. Johnson; office action issued Sep. 15, 2011.

(Continued)

*Primary Examiner* — Sanjay Cattungal
(74) *Attorney, Agent, or Firm* — Thorpe North & Western LLP

(57) ABSTRACT

A breast scanning system configured to scan a breast of a patient includes a table configured to receive the patient thereon. The table has an aperture formed therein configured to receive the breast of the patient pendant therethrough and positionable over and into a bath configured to contain a medium. An armature is movably disposable in the bath. The armature carries transducer arrays that are disposable in the bath, and configured to transmit and receive acoustic and/or ultrasound signals. A manual control is operatively coupled to the armature to manually move the armature and thus the transducer arrays within the bath.

24 Claims, 16 Drawing Sheets

U.S. PATENT DOCUMENTS

| | | | |
|---|---|---|---|
| 4,317,369 A | 3/1982 | Johnson | |
| 4,328,707 A | 5/1982 | Clement et al. | |
| 4,341,222 A | 7/1982 | Gardineer et al. | |
| 4,433,690 A | 2/1984 | Green et al. | |
| 4,485,819 A | 12/1984 | Igl | |
| 4,509,368 A * | 4/1985 | Whiting et al. | 73/624 |
| 4,594,662 A | 6/1986 | Devaney | |
| 4,662,222 A | 5/1987 | Johnson | |
| 4,727,550 A | 2/1988 | Chang et al. | |
| 4,798,209 A | 1/1989 | Klingenback et al. | |
| 5,078,142 A | 1/1992 | Siczek | |
| 5,227,797 A | 7/1993 | Murphy | |
| 5,305,757 A | 4/1994 | Unger et al. | |
| 5,339,815 A | 8/1994 | Liu et al. | |
| 5,474,072 A | 12/1995 | Shmulewitz | |
| 5,490,840 A | 2/1996 | Uzgiris et al. | |
| RE35,330 E | 9/1996 | Malone et al. | |
| 5,588,032 A | 12/1996 | Johnson et al. | |
| 5,609,152 A | 3/1997 | Pellegrino et al. | |
| 5,673,697 A | 10/1997 | Bryan et al. | |
| 5,677,893 A | 10/1997 | De Hoop et al. | |
| 5,696,848 A | 12/1997 | Pattie et al. | |
| 5,806,521 A | 9/1998 | Morimoto et al. | |
| 5,833,633 A | 11/1998 | Sarvazyan | |
| 5,985,850 A | 11/1999 | Falk et al. | |
| 5,999,836 A | 12/1999 | Nelson et al. | |
| 6,005,916 A | 12/1999 | Johnson et al. | |
| 6,019,724 A | 2/2000 | Gronningsaeter et al. | |
| 6,027,447 A | 2/2000 | Li | |
| 6,056,700 A | 5/2000 | Burney et al. | |
| 6,304,770 B1 | 10/2001 | Lee et al. | |
| 6,409,668 B1 | 6/2002 | Wollschlaeger | |
| 6,419,390 B1 | 7/2002 | Landis-Lowell | |
| 6,478,739 B1 | 11/2002 | Hong | |
| 6,480,565 B1 | 11/2002 | Ning | |
| 6,483,891 B1 | 11/2002 | Lazarev et al. | |
| 6,494,844 B1 | 12/2002 | Van Bladel et al. | |
| 6,544,186 B1 | 4/2003 | Shelby et al. | |
| 6,546,279 B1 | 4/2003 | Bova et al. | |
| 6,587,540 B1 | 7/2003 | Johnson et al. | |
| 6,587,590 B1 | 7/2003 | Pan | |
| 6,636,584 B2 | 10/2003 | Johnson et al. | |
| 6,693,558 B2 | 2/2004 | Hedrick | |
| 6,782,759 B2 | 8/2004 | Shank et al. | |
| 6,860,855 B2 | 3/2005 | Shelby et al. | |
| 6,925,317 B1 | 8/2005 | Samuels et al. | |
| 7,094,205 B2 | 8/2006 | Marmarelis | |
| 7,264,592 B2 | 9/2007 | Shehada | |
| 7,285,092 B2 | 10/2007 | Duric et al. | |
| 7,480,574 B2 | 1/2009 | Dubois et al. | |
| 7,551,708 B2 | 6/2009 | Basu et al. | |
| 7,570,742 B2 | 8/2009 | Johnson et al. | |
| 7,684,846 B2 | 3/2010 | Johnson et al. | |
| 7,699,783 B2 * | 4/2010 | Hanover et al. | 600/459 |
| 7,771,360 B2 * | 8/2010 | Johnson et al. | 600/459 |
| 7,841,982 B2 * | 11/2010 | Johnson et al. | 600/437 |
| 2002/0065461 A1 | 5/2002 | Cosman | |
| 2002/0131551 A1 | 9/2002 | Johnson et al. | |
| 2003/0097066 A1 | 5/2003 | Shelby et al. | |
| 2004/0034307 A1* | 2/2004 | Johnson et al. | 600/459 |
| 2004/0064046 A1* | 4/2004 | Shehada | 600/437 |
| 2004/0082856 A1 | 4/2004 | Marmarelis | |
| 2005/0143638 A1* | 6/2005 | Johnson et al. | 600/407 |
| 2006/0009693 A1* | 1/2006 | Hanover et al. | 600/407 |
| 2006/0009696 A1* | 1/2006 | Hanover et al. | 600/437 |
| 2006/0084859 A1 | 4/2006 | Johnson et al. | |
| 2006/0173304 A1* | 8/2006 | Wang | 600/437 |
| 2006/0287596 A1* | 12/2006 | Johnson et al. | 600/437 |
| 2006/0293597 A1* | 12/2006 | Johnson et al. | 600/437 |
| 2007/0282200 A1 | 12/2007 | Johnson et al. | |

FOREIGN PATENT DOCUMENTS

| | | |
|---|---|---|
| WO | WO99/55234 | 11/1999 |
| WO | WO02/082669 | 10/2002 |
| WO | WO2004/091369 | 10/2004 |

OTHER PUBLICATIONS

Hanover, U.S. Appl. No. 11/154,006, filed Jun. 15, 2005.
Hanover, U.S. Appl. No. 11/153,923, filed Jun. 15, 2005.
Hanover, U.S. Appl. No. 12/152,637, filed May 14, 2008.
Hanover, U.S. Appl. No. 10/821,407, filed Apr. 8, 2004.
Hanover, U.S. Appl. No. 11/223,910, filed Sep. 9, 2005.
Hanover, U.S. Appl. No. 11/222,541, filed Sep. 9, 2005.
Hanover, U.S. Appl. No. 11/223,084, filed Sep. 9, 2005.
Hanover, U.S. Appl. No. 11/436,989, filed May 17, 2006.
Hanover, U.S. Appl. No. 11/437,001, filed May 17, 2006.
U.S. Appl. No. 11/153,923, filed Jun. 15, 2005; Barry K. Hanover; office action issued Oct. 15, 2010.
MacDonald, Calum et al., "Nonlinear Seismic Inversion", Abstract of presentation made at 54th Annual Meeting and Exposition of the Society of exploration Geophysicists at Atlanta, Ga., Dec. 2-6, 1984, pp. 655-657.
P.R. Williamson, "Tomographic inversion in reflection seismology," Geophys. J. Int. 100, pp. 255-274, 1990.
W.W. Kim et al., Accelerated Inverse Scattering Algorithms for Higher Contrast Objects, in 1987 IEEE Ultrasonics Symposium, 903-906, (IEEE Cat. No. 87ch2492-7).
S.J. Norton, "Iterative Seismic Inversion," Geophysical Journal, No. 94, pp. 457-468 (1988).
T.K. Sarkar, et al., (1986) "Application of FFT and the Conjugate Gradient Method for the Solution of Electromagnetic Radiation from Electrically Large and Small Conducting Bodies," IEEE Trans. Antennas Propagat., vol. AP-34, pp. 635-640, May.
R.J. Wombell and M.A. Fiddy (1988), "Inverse Scattering Within the Distorted-wave Born Approximation," Inverse Problems 4 (1988).
Y. Zhou et al., "Constrained Reconstruction of Object Acoustic Parameters from Noisy Ultrasound Scattering Data," Proc. of the IEEE 1987 Ultrasonics Symposium pp. 897-901 (1987).
Kostas T. Ladas and A. J. Devaney, "Iterative Methods in Geophysical Diffraction Tomography," Inverse Problems 8 (1992).
M.J. Berggren, et al., "Acoustic Inverse Scattering Images from Simulated Higher Contrast Objects and from Laboratory Test Objects," Acoustical Imaging 16, Chicago, Illinois, Jun. 1987.
Brent S. Robinson and James F. Greenleaf, "An Experimental Study of Diffraction Tomography Under the Born Approximation," Acoustical Imaging vol. 18, 1991. pp. 391-400.
M.J. Berggren et al., "Performance of Fast Inverse Scattering Solutions for the Exact Helmholtz Equation Using Multiple Frequencies and Limited Views," pp. 193-201, 1987.
W.W. Kim et al., "Analysis of Inverse Scattering Solutions from Single Frequency, Combined Transmission and Reflection Data for the Helmholtz and Riccati Exact Wave Equations," Acoustical Imaging 15, pp. 359-369, Plenum Press (1987).
E.J. Ayme-Bellegarda et al., "Forward Ultrasonic Scattering from Multidimensional Solid or Fluids Inclusions Buried in Multilayered Elastic Structures," IEEE Trans. Ultras., Ferro., and Freq. Cont., vol. 39, No. 1, Jan. 1992.
E.J. Ayme-Bellegarda and T.M. Habashy, "Ultrasonic Inverse Scattering of Multidimensional Objects Buried in Multilayered Elastic Background Structures," IEEE Transactions on Ultrasonics, Ferroelectics, and Frequency Control, vol. 39, No. 1, Jan. 1992.
J.K. Cohen and F.G. Hagin, "Velocity Inversion Using a Stratified Reference," Geophysics, vol. 50, 11, 1985 pp. 1689-1700.
E. Crase et al., "Robust Elastic Nonlinear Waveform Inversion: Application to Real Data," Geophysics, vol. 55, No. 5 (May 1990) pp. 527-538.
Peter Mora, "Nonlinear Two-dimensional Elastic Inversion of Multioffset Seismic Data," Geophysics, vol. 52, No. 9, Sep. 1987.
G.S. Pan et al., "Full-waveform Inversion of Plane-wave Seismograms in Stratified Acoustic Media: Theory and Feasibility," Geophysics, vol. 53, No. 1 (1988). pp. 21-31.
G.R. Franssens, "Calculation of the Elasto-dynamic Green's Function in Layered Media by Means of a Modified Propagator Matrix Method," Geophys. J.R. astr. Soc. 1983 75, pp. 669-691.
B.L.N. Kennett and N.J. Kerry, "Seismic Waves in a Stratified Half Space," Geophys. J.R. astr. Soc. 57, pp. 557-583, 1979.
Lines, Larry R. et al., "Inversion with a Grain of Salt," Abstract of presentation made at 54th Annual Meeting and Exposition of the Society of Exploration Geophysicists at Atlanta, Ga., Dec. 2-6, 1984, pp. 638-640.

Johnson, S.A. et al., (1984) "Inverse Scattering Solutions by a Sinc Basis. Multiple Source Moment Method—Part III: Fast Algorithms." Ultrasonic Imaging 6, pp. 103-116.

Johnson S.A. et al., (1983) "Inverse Scattering Solutions by a Sinc Basis, Multiple Source, Moment Method—Part I: Theory." Ultrasonic Imaging 5, 361-375.

Johnson, S.A. et al., (1983) "Acoustical Inverse Scattering Solutions by Moment Methods and Backpropagation." in Conference on Inverse Scattering: Theory and Application. SIAM, Philadlephia. pp. 144-155.

La Bras, L. et al., "Presentation of a Born Inversion for Multioffset Reflection Data: Tests on Synthetic Seismograms," Abstract of presentation made at 54th Annual Meeting and Exposition of the Society of Exploration Geophysicists at Atlanta, Ga., Dec. 2-6, 1984.

Lailly, P., "Migration Methods: Practical but Efficient Solutions to the Seismic Inverse Problem," Inverse Problems of Acoustic and Elastic Waves, pp. 182-214.

Kaman, E. J., "Detailed Inversion of Reservoir Data by Constrained Parameter Estimation and Resolution Analysis," Abstract of presentation made at 54th Annual Meeting and Exposition of the Society of Exploration Geophysicists at Atlanta, Ga., Dec. 2-6, 1984. pp. 652-655.

Johnson, Steven A. et al., "Ultrasound Tomography by Galerkin or Moment Methods", Lecture Notes in Medical Informatics, (1984) vol. 23, pp. 254-276.

Tarantola, A. et al., "Inverse Problems: Quest of Information", J. Geophysics, vol. 50, No. 3, pp. 159-170 (1982).

Verwest, B. J. et al., "Prestack Inversion of Plane-Layered Viscoacoustic Earth Parameters," Abstract of presentation at 54th Annual Meeting and Exposition of the Society of the Exploration Geophysicist at Atlanta, Ga., Dec. 2-6, 1984.

Carrion, Philip M. et al., A Method for Computation of Velocity Profiles by Inversion of Large-Offset Records; Geophysics, (1984) pp. 1249-1258 vol. 49, No. 8.

Cheng, Guan and Shimon Coen, The Relationship between Born Inversion, Rytov Inversion, and Migration for Both CMP Stacked and Slant Stacked Data, Abstract of presentation made at 54th Annual Meeting & Exposition of the Society of Exploration Geophysicists, Atlanta, Dec. 2-6, 1984 pp. 575-579.

Tarantola, A., "Linearized Inversion of Seismic Reflection Data," Geophysical Prospecting, vol. 32, pp. 998-1015 (1984).

De Figueiredo, Rui J.P., "Approximation-Theoretic Methods for Nonlinear Deconvolution and Inversion", Information Sciences, pp. 209-220 (1983) vol. 31, No. 3.

Foster, Douglas J. et al., "Linear Inversion Applied to Real Seismic Data", Abstract of presentation made at the 54th Annual Meeting & Exposition of the Society of Exploration Geophysicists, Atlanta, Dec. 2-6, 1984.

Tarantola, Albert et al., "Nonlinear Inversion of Seismic Reflection Data", Abstract of presentation made at the 54th Annual Meeting & Exposition of the Society of Exploration Geophysicists held at Atlanta, Dec. 2-6, 1984, pp. 645-658.

Goutsias et al., "A 2-D Stochastic Earth Model for Seismic Inversion", Abstract of presentation made at the 54th Annual Meeting and Exposition of the Society of Exploration Geophysicists held at Atlanta, Ga., Dec. 2-6, 1984, pp. 385-386.

Greenleaf, James F., edited by D. W. McLaughlin Computer Tomography from Ultrasound Scattered by Biological Tissues, SIAM-AMS Proceedings (1984) pp. 53-63.

Hanson, Douglas W., "Multiparameter Seismic Inversion of Noisy Data", Abstract of presentation made at the 54th Annual Meeting and Exposition of the Society of Exploration Geophysicists held at Atlanta, Ga., Dec. 2-6, 1984.

Harkrider, David G., "Synthetics and Theoretical Seismology", Reviews of Geophysics and Space Physics, (1983) vol. 21, No. 6, pp. 1299-1308.

McClary, W. Keith, "Fast Seismic Inversion", Geophysics, (1983) vol. 48, No. 10, pp. 1371-1372.

Morley, Lawrence C., "Invertibility of Elastic Layered Earth Parameters from Precritical P-Wave Reflection Amplitudes", Abstract of presentation at 54th Annual Meeting and Exposition of the Society of Exploration Geophysicists at Atlanta, Ga., Dec. 2-6, 1984, pp. 641-643.

Nercessian, A., "Linearized Inversion of Multioffset Seismic Reflection Data," Abstract of presentation at 54th Annual Meeting and Exposition of the Society of Exploration Geophysicists at Atlanta, Ga., Dec. 2-6, 1984.

P. D. Corl et al., "A Digital Synthetic Focus Acoustic Imaging System", Acoustical Imaging, 8th Int'l. Conference, Jun. 1978, pp. 39-53.

S. A. Johnson et al., High Resolution Ultrasound Echo and Reconstruction Imaging from Temporal and Spatial Projections by Adaptive Ray Tracing, Proceedings of the 4th International Joint Conference Pattern Recognition, Feb. 1978 pp. 846-850.

S. A. Johnson et al., Quantitative Synthetic Aperture Reflection Imaging Correction for Refraction and Attenuation: Appl. Seismic Tech. in Medicine, Feb. 1978, pp. 337-349.

S. A. Johnson et al., Ultrasound Images Corrected for Refraction and Attenuation: Comparison of New High Resolution Methods, Aug. 1979, pp. 55-71.

S. A. Johnson, et al., "Algebraic and Anly. Inversion Acou. Data Partially or Fully Enclosing Apertures", Acoustical Imaging, pp. 577-598, Jun. 1978.

Sigalov, Ya. B. et al., "On the Solution of the Two-Dimensional Inverse Dynamic Problem of Seismometry by the Finite-Difference Method, Part 1." Geophysical Journal, vol. 5, No. 4, pp. 508-521 (1984).

Tarantola, A. et al., "Generalized Nonlinear Inverse Problems Solved Using the Lease Squares Criterion," Review of Geophysics and Space Physics, vol. 20, No. 2, pp. 219-232 (1982).

Tarantola, A., "Inversion of Seismic Reflection Data in the Acoustic Approximation", Geophysics, vol. 49, No. 8, pp. 1259-1266 (1984).

Johnson, S. A. et al., "Fast Iterative Algorithms for Inverse Scattering Solutions of the Helmholtz and Riccati Wave Equations", Acoustical Imaging, vol. 13, pp. 75-87.

U.S. Appl. No. 12/152,637, filed May 14, 2008; Steven A. Johnson; notice of allowance issued Apr. 27, 2012.

\* cited by examiner

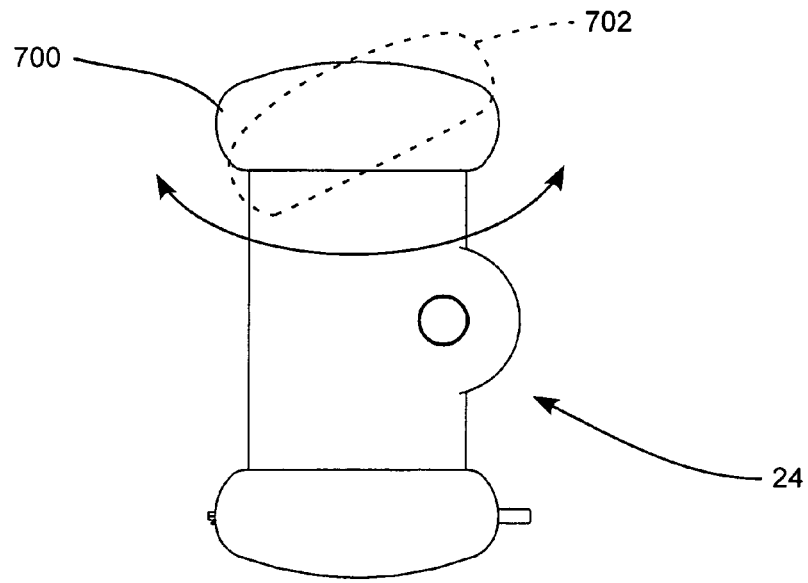
FIG. 17
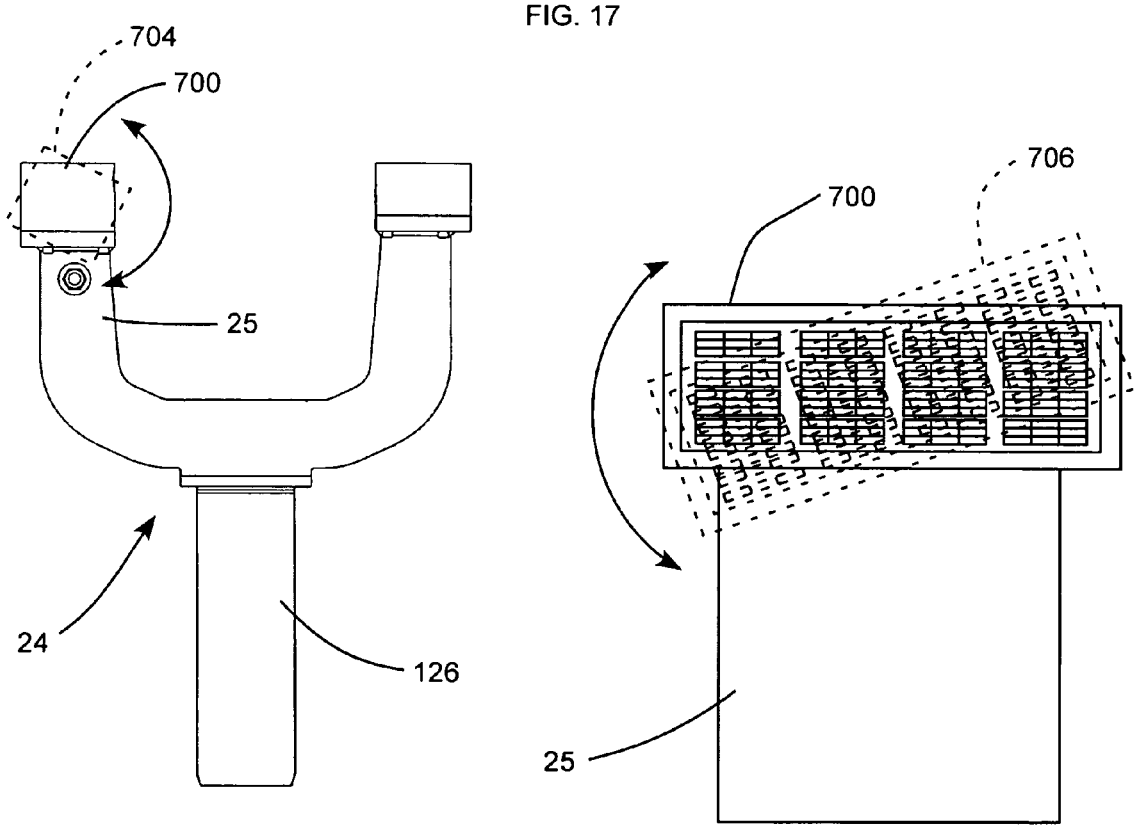
FIG. 18
FIG. 19

BREAST SCANNING SYSTEM

PRIORITY CLAIM

Benefit is claimed of U.S. Provisional Patent Application No. 60/930,377, filed May 15, 2007, and U.S. Provisional Patent Application No. 60/930,413, filed May 15, 2007, which are herein incorporated by reference in their entirety for all purposes.

BACKGROUND OF THE INVENTION

1. Field of the Invention

The present invention relates generally to a breast scanning system.

2. Related Art

Other than skin cancer, breast cancer is the most common cancer among women, and is the second leading cause of cancer death in women, after lung cancer. According to the American Cancer Society, about 215,990 women in the United States will be found to have invasive breast cancer in 2004, and about 40,110 women will die from the disease.

Approximately 44.5 million women in the United States are screened for breast cancer each year with 10% or 4.5 million referred for a second diagnostic test. The latest American Cancer Society Breast Cancer Statistics report indicates that 1 in 7 women will get breast cancer during her lifetime. The current standard of care has significant problems, generating unacceptably high rates of false positive tests—between 8% and 10%—and upwards of 15% false negative tests. The result is that many women suffer from unnecessary and invasive biopsies. In addition, each year the U.S. healthcare system spends an estimated $2.1 billion on biopsies, which yield negative results more than 75% of the time.

Breast cancer is a malignant tumor that has developed from cells of the breast. A malignant tumor is a group of cancer cells that may invade surrounding tissues or spread (metastasize) to distant areas of the body. The female breast is made up mainly of lobules (milk-producing glands), ducts (milk passages that connect the lobules to the nipple), and stroma (fatty tissue and connective tissue surrounding the ducts and lobules, blood vessels, and lymphatic vessels). Lymphatic vessels are like veins, except that they carry lymph instead of blood. Lymph is a clear fluid that contains tissue waste products and immune system cells (cells that are important in fighting infections). Lymph nodes are small bean-shaped collections of immune system cells that are found along lymphatic vessels. Cancer cells can enter lymphatic vessels and spread to lymph nodes. Most lymphatic vessels in the breast connect to lymph nodes under the arm (axillary lymph nodes). Some lymphatic vessels connect to lymph nodes inside the chest (internal mammary nodes) and either above or below the collarbone (supra- or infraclavicular nodes). When breast cancer cells reach the axillary (underarm) lymph nodes, they may continue to grow, often causing the lymph nodes in that area to swell. If breast cancer cells have spread to the underarm lymph nodes, they are more likely to have spread to other organs of the body as well. Thus, it is important to find out if breast cancer has spread to the axillary lymph nodes when choosing a treatment.

Most breast lumps are not cancerous, that is, they are benign. Most lumps turn out to be fibrocystic changes. The term "fibrocystic" refers to fibrosis and cysts. Fibrosis is the formation of fibrous (or scar-like) connective tissue, and cysts are fluid-filled sacs. Fibrocystic changes can cause breast swelling and pain. This often happens just before a period is about to begin. The breast may feel nodular, or lumpy, and, sometimes, a clear or slightly cloudy nipple discharge is noticed. Benign breast tumors such as fibroadenomas or papillomas are abnormal growths, but they are not cancer and cannot spread outside of the breast to other organs. They are not life threatening.

Although widespread use of screening mammography has increased the number of breast cancers found before they cause any symptoms, some breast cancers are not found by mammography, either because the test was not done or because even under ideal conditions mammography cannot find every breast cancer. The most common sign of breast cancer is a new lump or mass. A painless, hard mass that has irregular edges is more likely to be cancerous, but some rare cancers are tender, soft, and rounded. An elliptical mass with its major axis perpendicular to skin line or to natural internal tissue planes (or penetrating such planes), is a danger signal that requires further investigation. For this reason, it is important that a health care professional who is experienced in diagnosing breast diseases check any new breast mass or lump.

Other signs of breast cancer include a generalized swelling of part of a breast (even if no distinct lump is felt), skin irritation or dimpling, nipple pain or retraction (turning inward), redness or scaliness of the nipple or breast skin, or a discharge other than breast milk. Sometimes a breast cancer can spread to underarm lymph nodes even before the original tumor in the breast tissue is large enough to be felt.

If there is any reason to suspect breast cancer, other tests must be performed. After a complete physical exam (including a clinical breast exam), doctors often recommend a diagnostic mammogram or a breast ultrasound. A clinical breast examination (CBE) is an exam of the breasts by a health professional, such as a doctor, nurse practitioner, nurse, or physician assistant. The examiner first looks at the breasts for changes in size or shape. Then, using the pads of the finger tips, the breasts are felt for lumps.

Although mammograms are mostly used for screening, they can also be used to examine the breast of a woman who has a breast problem. This can be a breast mass, nipple discharge, or an abnormality that was found on a screening mammogram. In some cases, special images known as cone views (or spot views) with magnification are used to increase contrast and thus make a small area of altered breast tissue easier to evaluate. A diagnostic mammogram may show that a lesion (area of abnormal tissue) has a high likelihood of being benign (not cancer). In these cases, it is common to ask the woman to come back sooner than usual for a recheck, usually in 4 to 6 months. On the other hand, a diagnostic mammogram may show that the abnormality is not worrisome at all, and the woman can then return to having routine yearly mammograms. Finally, the diagnostic work-up may suggest that a biopsy is needed to tell if the lesion is cancer.

Ultrasound, also known as sonography, uses high-frequency sound waves to outline a part of the body and to visualize internal organs and tissue. High-frequency sound waves are transmitted into the area of the body being studied and echoed back. A computer or dedicated electronic circuitry picks up the sound wave echoes and changes them into an image that is displayed on a computer screen. Breast ultrasound is sometimes used to evaluate breast abnormalities that are found during mammography or a physical exam. One of the most common abnormalities that women have is fibrocystic disease. Ultrasound is useful for detecting fibrocystic disease. It is the easiest way to tell if a cyst is present without placing a needle into it to draw out fluid. It can also find some breast masses. Conventional medical ultrasound uses a single ultrasound array to both transmit and receive echoes and thereby measure the ultrasound reflectivity and distance of various objects under the skin surface. It assumes that the speed of sound is constant through the tissue being imaged. It has difficulty imaging objects with low reflectivity or high absorption of sound. It produces images which are typically two-dimensional, distorted, grainy, and contain speckle. Foreground objects tend to mask deeper structures (e.g. cast shadows on).

A biopsy is done when mammograms, ultrasound, or the physical examination finds a tumor. A biopsy is the only way to tell if cancer is really present. All biopsy procedures remove a tissue sample for examination under a microscope. There are several types of biopsies, such as fine needle aspiration biopsy, core (large needle) biopsy, and surgical biopsy. Biopsies are often done under ultrasound or MRI guidance. Each type of biopsy has distinct advantages and disadvantages. The choice of which to use will depend on the specific situation. Some of the factors the doctor will consider include how suspicious the lesion appears, how large it is, where in the breast it is located, how many lesions are present, other medical problems the patient may have, and the patient's personal preferences. Statistically, three of four biopsies are benign.

SUMMARY OF THE INVENTION

It has been recognized that it would be advantageous to develop a system and method to facilitate diagnosis of breast cancer and reduce unnecessary biopsies through improved and advanced tomography or ultrasonic scanning.

The invention provides a breast scanning system configured to scan a breast of a patient and includes a transmitter array configured to transmit acoustic signals through the breast. A receiver array can be positioned to receive acoustic signals from the transmitter array to obtain transmission attenuation data. A reflection array can be disposed laterally between the transmitter array and the receiver array. The reflection array can be configured to transmit acoustic signals through the breast and receive reflected acoustic signals from the breast to obtain reflection data from the breast.

In another aspect, the breast scanning system can include a table configured to receive the patient. The table can have an aperture configured to receive the breast of the patient pendant through the aperture and positionable over and into a bath configured to contain a medium.

In yet another aspect, the breast scanning system can include means for combining the transmission and/or speed of sound data from the transducer arrays and reflection data from the reflection array into an image of the breast of the patient.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 17 is a top view of opposing transducer arrays with one of the arrays pivoted about a vertical axis;

FIG. 18 is a side view of opposing transducer arrays with one of the arrays pivoted about a horizontal axis;

FIG. 19 is a side view of opposing transducer arrays with one of the arrays pivoted about a horizontal axis;

DETAILED DESCRIPTION

Figure 1:
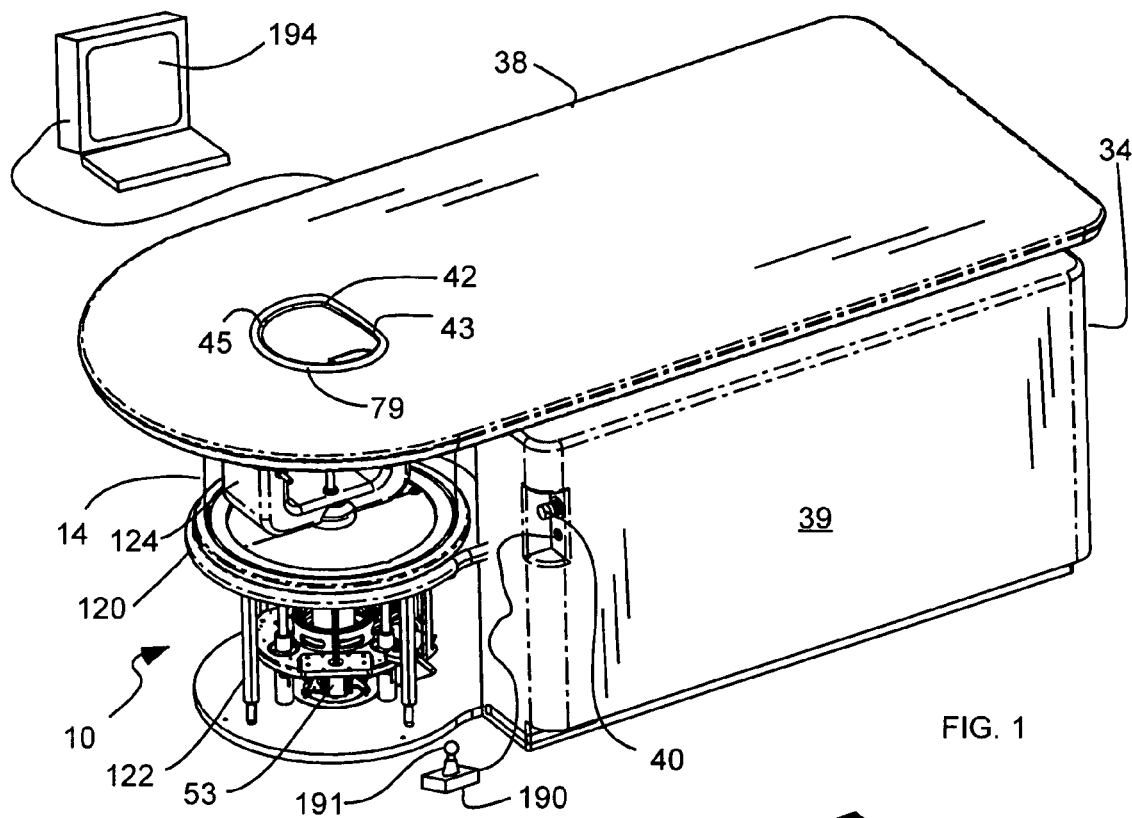
FIG. 1 is a perspective view of a breast scanning system in accordance with an embodiment of the present invention, shown with a table in a lowered position.
Figure 2:
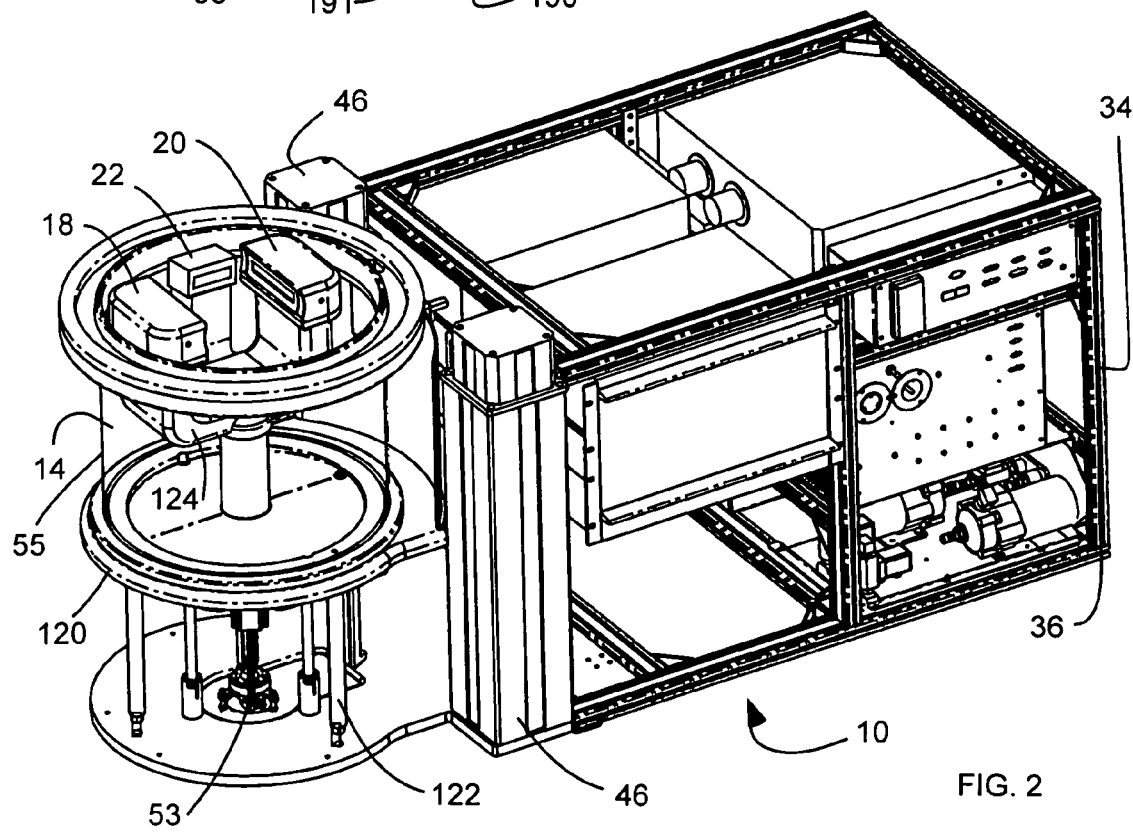
FIG. 2 is a partial perspective view of the breast scanning system of FIG. 1 with the table and outer skin or skirt removed.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1-7, a breast scanning and/or imaging system, indicated generally at 10, in accordance with the present invention is shown for use in the diagnosis of breast cancer. The system can be a non-invasive, diagnostic tool to provide detailed information about the physiology (i.e. bulk tissue properties) and anatomy (i.e. physical architecture) of the human female breast. The system may be used as an adjunct to mammography to aid physicians in diagnosing breast cancer by providing information about tissue properties that help to more clearly differentiate normal or benign form malignant tissue in the breast. The system may replace other diagnostic testing, such as diagnostic mammograms, breast ultrasound, and other imaging technologies currently used between a screening mammogram and a biopsy.

In general, the system 10 can use a non-intrusive/non-invasive acoustics inspection technique utilizing ultrasound inverse scattering technology to produce a 3-D stack of tomography (2-D planar slice) images (similar in appearance and spatial resolution to CT or MR imaging methods). It will be appreciated that while acoustic inspection techniques utilizing ultrasound are described in detail in this application, acoustic inspection techniques utilizing other sound based pressure waves, such as infrasound waves or audible sound waves, can also be used to accomplish the imaging and analysis conceived and described herein.

Direct 3-D imaging is a further feature of the system 10. These images can be produced using two different techniques, namely Ultrasound Reflective Tomography (URT) and Ultrasound Inverse Scattering Tomography (UIST). Compared with conventional projection mammography, URT images can be more detailed, easier to read, and do not use potentially harmful ionizing radiation. Unlike conventional ultrasound, ultrasound images using inverse scattering technology completely penetrate and sample the entire breast for uniformity and better overall resolution. In addition, such images are absolute quantitative representations of ultrasound tissue properties, and therefore yield values which can be compared to other tissues suspected to be of similar type. The scan which results in these images is automated, thus reducing the dependence on the system operator for image quality and consistency. The images can be reconstructed in three dimensions providing an important visualization tool for diagnosis, biopsy and surgery staging.

The system 10 can use a plurality of ultrasound and/or acoustic arrays that rotate around the breast, generating true 3-D images and diagnostic information in a commercially viable timeframe, such as less than 20 minutes per exam. The breast (shown in phantom lines at 41 in FIG. 7) can be disposed in a bath 14 of medium, such as liquid, water or gel. The use of water will be described throughout for illustrative purposes; however, other mediums can be used in order to approximately match acoustic properties of the medium with the acoustic properties of the breast tissue. For example, more viscous or dense mediums, such as oils, gels or the like, can also be used in the bath so as to match the acoustic wave attenuation, acoustic wave speed, density, and other acoustic properties affecting the transfer and distribution of acoustic energy in the breast.

In one aspect, the system 10 can include two opposing ultrasound transducer arrays 18, 20 (FIG. 7) movably disposed in the bath 14 to obtain both reflection and transmission information used to generate images and diagnostic information. One of the arrays can be a transmitting array 18 and the opposing array can be a receiving array 20. In another aspect, the system 10 can include three arrays, with two opposing arrays 18 and 20. The two opposing arrays can transmit and receive acoustic signals through the breast. Thus, one of the arrays 18 can be a transmitter array that can transmit acoustic signals through the breast, and the opposing array 20 can be a receiver array positioned to receive acoustic signals from the transmitter array in order to obtain transmission attenuation data. The third array can be a reflection array 22.

The reflection array 22 can be oriented to transmit, receive, or reflect acoustic waves perpendicular or transverse to the acoustic waves, pulses or wave-fronts of the two opposing arrays. The transverse reflection array 22 can be a reflection array disposed laterally between the transmitter array and the receiver array. The reflection array 22 can transmit acoustic signals through the breast and receive reflected acoustic signals from the breast to obtain reflection data from breast.

The transmission speed of sound and/or attenuation data from the transmission and receiver arrays 18 and 20 can be combined with the reflection data from the reflection array 22. The data can be used to generate images and diagnostic information of the breast. A micro-electronic processor disposed in a computer 194 can be configured to process and combine the data from the arrays 28, 20, and 22. Such a micro-electronic processor is one means for combining the data from the arrays to form an image of the breast.

The arrays 18, 20 and 22 can be mechanically designed to rotate and move up and down with respect to the patient's breast in order to generate a complete 3-D data set for the area of interest in the breast, or even for the entire breast. Advantageously, each of the arrays 18, 20 and 22 can be designed to rotate or move upward or downward independently from the other arrays. The arrays 18, 20 and 22 can also rotate or move similar or complementary to the other arrays. Thus, in one aspect, the two opposing arrays 18 and 20 can rotate, tilt or pivot in concert, while the transverse reflection array 22 moves independent from the two opposing arrays.

In this way, the two opposing arrays 18 and 20 can be positioned to scan a portion of the breast either at a relatively parallel orientation with respect to the chest wall of the patient, in which each of the two opposing arrays are substantially co-planar. Additionally, the two opposing arrays 18 and 20 can scan a portion of the breast at a relative incline or angle with respect to the chest wall, in which one of the two opposing arrays 18 and 20 is positioned closer to the chest wall and the other is positioned closer to the nipple of the breast. In this latter case, it will be appreciate that the arrays 18 and 20 can also tilt with respect to the chest wall of the patient, so as to achieve a desired inclination or angle relative to the chest wall. The transverse reflection array 22 can be positioned at any distance from and at any angle and/or tilt with respect to the chest wall independent of the two opposing arrays 18 and 20, so as to be able to provide additional detail with respect to an area of concern in the patient's breast tissue.

Acoustic and/or ultrasound pulses can be emitted from transducer emitters 100 in the arrays, and can be used for two imaging modalities: reflective and transmissive. For reflective images, the system emits a pulse from one array and receives the reflected energy back in the same array. The array can emit a pulse at 60 positions (every 6 degrees) around the breast. During the same rotation sequence, the transmitter array 18 can emit an ultrasound signal into and through the breast at 180 different locations (every 2 degrees) around the entire breast. The resulting waveforms are received by the opposing receiver array 20. This allows the system 10 to simultaneously generate data for both reflection and transmission sound properties of the breast. Alternatively, the arrays 18 and 20 can move to more than 180 positions and/or emit continuously.

The imaging system 10 produces three separate images using two different imaging techniques: 1) transmission information generates images representing bulk tissue properties of speed of sound and attenuation of sound at each point in the breast; and 2) data generated from reflection information generates detailed reflective tomographic images that are refraction corrected. These imaging techniques are combined to effectively produce a three-dimensional stack of "slices" of the breast. Data from the ultrasound source is analyzed, and a quantitative map of tissue properties is rendered. In the "transmission mode" the energy propagates through the breast (or other soft tissue). In the "reflection mode", the energy reflects back to the receivers. In both cases, the energy of the acoustic wave is refracted and scattered from the tissue it encounters. In this process multiple physical phenomena take place: reflection, refraction, diffraction, and multiple scattering events. These effects are generally ignored in present ultrasound, which seriously degrades the image, therefore rendering it useful only in differentiating architectural or structural properties within the breast. In present ultrasound it is impossible to acquire quantitative acoustic tissue values at a level sufficient for diagnosis of tissue characteristics using standard reflection ultrasound or imaging.

Further details of inverse scattering technology and imaging are disclosed in U.S. Pat. Nos. 4,662,222; 5,339,282; 6,005,916; 5,588,032; 6,587,540 and 6,636,584, which are herein incorporated by reference in their entirety.

The bath 14 can be supported by or disposed on a base 34. The base 34 can include a framework 36 and can contain various components of the system, as described in greater detail below. A skin or skirt 39 can be disposed around the base, or portions thereof, to protect and restrict access to the various components. The bath 14 can be disposed at one end of the system or base 34 to increase the viewing angle or viewing perimeter. The base 34 can include controls, such as an emergency shut-off or stop button 40. In addition, the base 34 can include various input/output connections, such as for controls 190.

A horizontal table 38 can be disposable over the bath 14 and the base 34 to receive the patient thereon. The table 38 can be rigid, but can have a padded upper surface for patient comfort. The table 38 can also be supported or carried by the base 34. An aperture 42 can be formed in the table 38 and positionable over the bath 14. In use, the patient's breast is received pendant through the aperture (as shown in phantom lines in FIG. 7), and into the bath 14. The aperture 42 can be located nearer one end of the table 38. The end of the table 38 with the aperture 42 can be broadly curved to circumscribe the bath 14 and/or the aperture 42. The curved end of the table 38 facilitates access to the bath and/or breast, and facilitates viewing the bath and/or breast.

Figure 5:
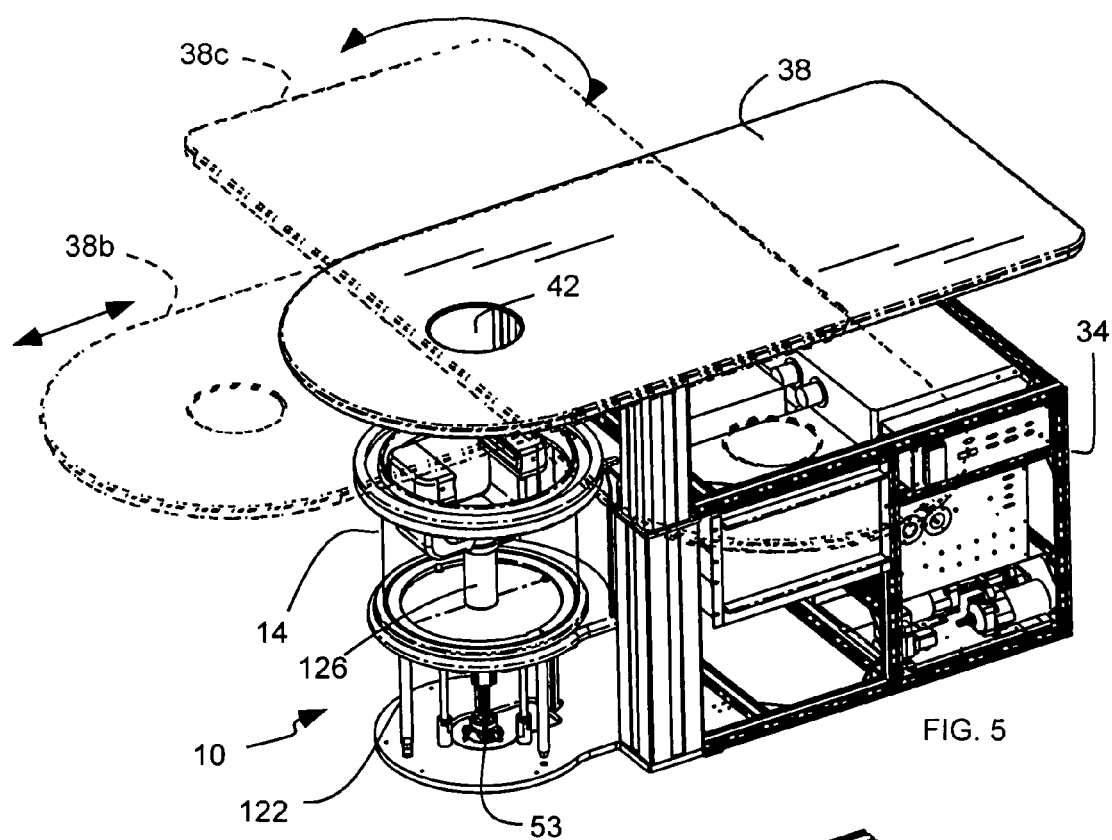
FIG. 5 is a perspective view of the breast scanning system of FIG. 1, shown with the table in the raised position, shown with the outer skin or skirt removed.

The aperture 42 can be any size and shape as required to fit the breast of the patient. In one aspect, the aperture 42 can be substantially circular (FIG. 5). In another aspect, the aperture 42 can be D-shaped having a straight edge 43 and a semicircular edge 45 extending from the straight edge, as shown in FIG. 1. The straight edge 43 of the D-shaped aperture 42 can pull the breast away from the chest wall of the patient so as to reduce other areas of the body from entering the aperture.

Additionally, a seal can be formed between the table 38 and the bath 14 and another seal can be formed between the skin of a patient and the table 38 around the aperture 42 such that the bath 14 becomes a sealed enclosure containing the breast 41. A vacuum 77 (FIG. 3) can be fluidly coupled to the bath 14 and can be used to create a vacuum pressure inside the bath in order to draw the breast 41 further into the bath 14 and away from the chest wall of the patient. The vacuum is one means for extending or drawing breast tissue into the bath and away from the wall of the chest of the patient in order to allow acoustic signals from the arrays 18, 20 and 22 to pass through the extended breast tissue.

Another means for extending the breast tissue into the bath 14 can include a relatively high friction surface 79 surrounding the aperture 42, as shown in FIG. 1. As the breast is placed through the aperture 42, the skin can contact the friction surface 79 and the friction surface can resist movement of the skin through the aperture 42. The operator can then pull the breast further through the aperture 42 and the friction surface 79 can act to hold the breast in the extended position.

Figure 3:
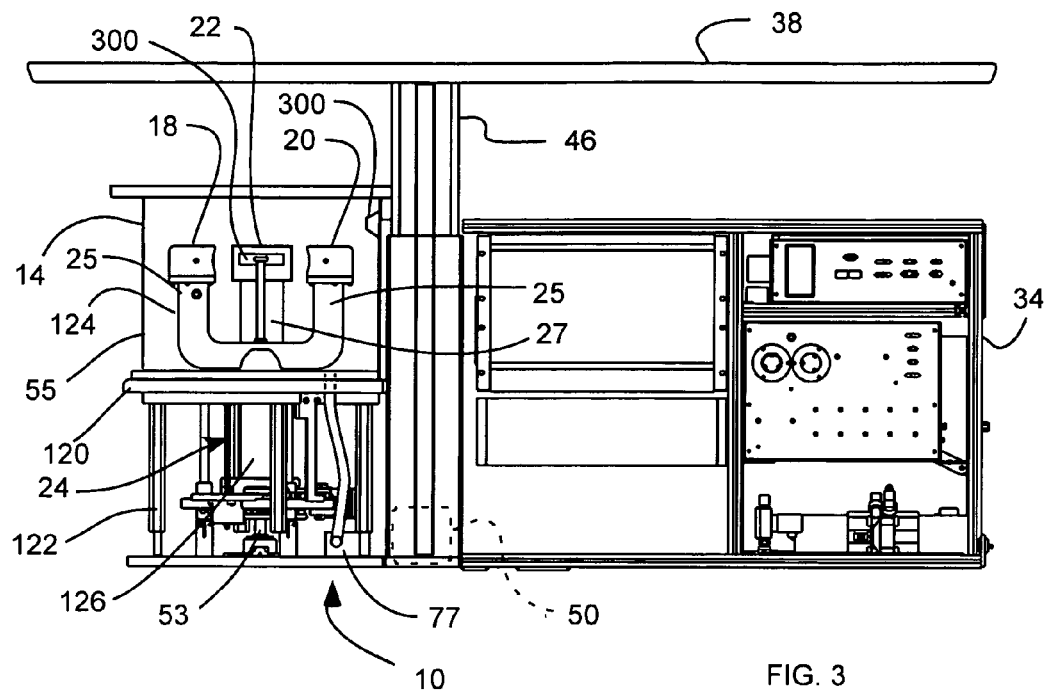
FIG. 3 is a partial side view of the breast scanning system of FIG. 1, shown with the table in a raised position and the outer skin or skirt removed.

It will be appreciated that the area of the breast near the chest wall is difficult to position within a scanning device. Thus, the D-shaped aperture 42, as shown in FIG. 1, the vacuum 77 as shown in FIG. 3, and the friction surface 79, shown in FIG. 1, provide the advantage of capturing more of the breast tissue in the scan. Other aperture shapes, such as oval or V-shaped apertures can also be used to move the breast into optimal scanning positions. In addition, the shape of the aperture 42 and friction surfaces 79 can resist other body parts, such as the stomach or abdomen, from entering the aperture 42 and interfering with the scan of the breast.

Figure 4:
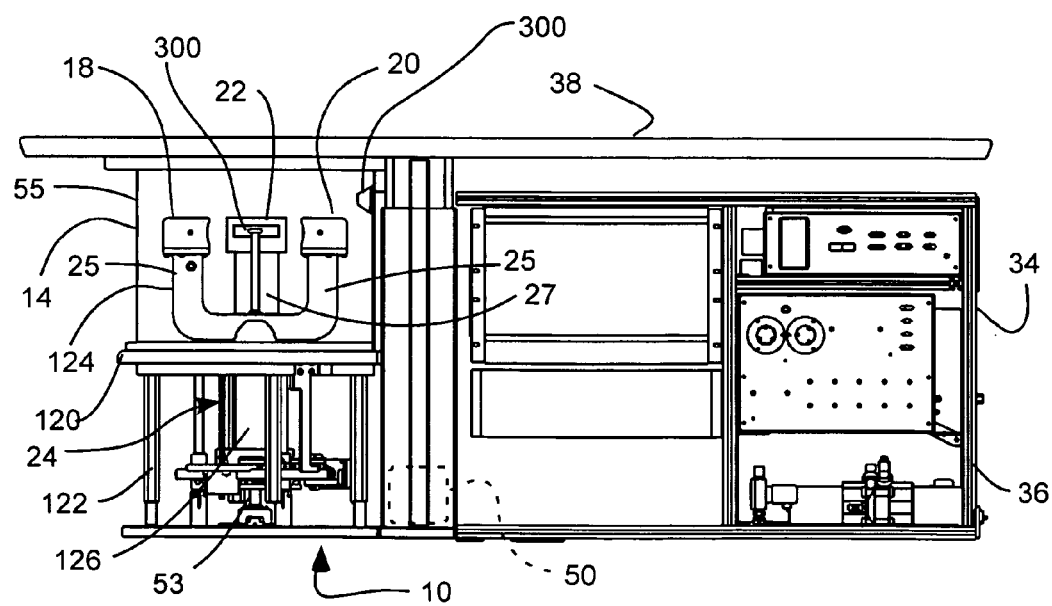
FIG. 4 is a partial side view of the breast scanning system of FIG. 1, shown with the table in the lowered position and the outer skin or skirt removed.

The table 38 and the bath 14 can be linearly vertically displaceable with respect to one another. For example, the table 38 can be movable upward and downward, away from and towards the bath. The table 38 can have a lowered position, as shown in FIGS. 1 and 4, and a raised position, as shown in FIG. 3. In the lowered position (FIGS. 1, 4), the table 38 is adjacent the bath 14 to position the breast within the bath. In the raised position (FIG. 3), the table 38 is spaced-above the bath 14 to elevate the breast above the bath. The raised position allows access to the breast by a technician or physician. For example, a technician can center the breast in the aperture 42, and/or draw the breast further through the aperture 42.

One or more columns 46 can support the table 38. For example, a pair of columns 46 can be disposed on each side of the base 34. The columns 46 can be telescoping columns such that one or more motors 50 can be coupled to the columns 46 to raise and lower the columns, and thus the table. The motors 50 can be located within the columns 46, and can be rotational motors providing relative rotational movement between a threaded screw and a threaded nut to provide linear motion. The column(s) 46 and motors 50 are one example of means for maintaining the table in the raised position with the table spaced-above the bath, and means for raising and lowering the table.

Figure 6:
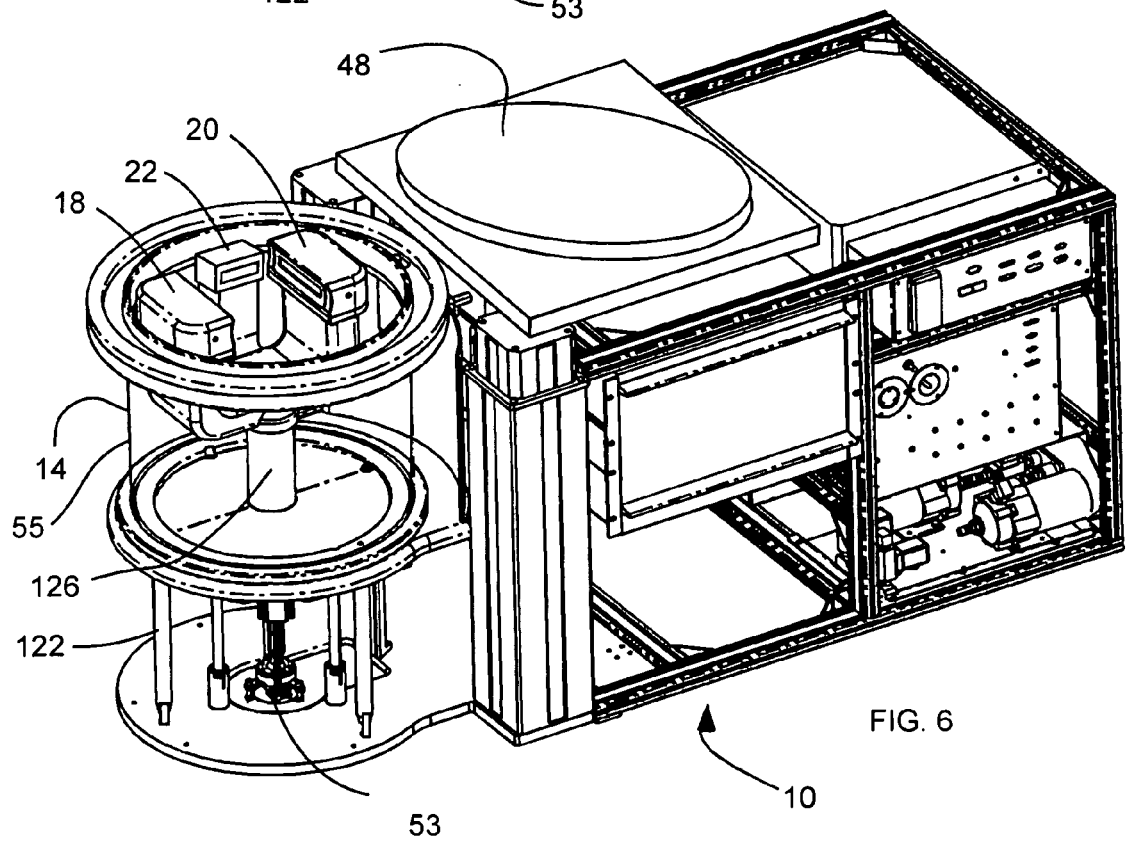
FIG. 6 is a partial perspective view of the breast scanning system of FIG. 1, shown with the table and outer skin or skirt removed.

Referring to FIGS. 5 and 6, the table 38 can also be displaceable horizontally, as shown in dashed lines, so that the aperture 42 can be displaced away from the bath 14 to allow further access to the breast for additional procedures, such as biopsies. For example, the table 38 can be linearly displaceable, such as longitudinally in a forward direction, indicated by 38*b*. A linear slider can be disposed between the columns and the table to allow the table to slide. As another example, the table 38 can be rotationally or pivotally disposed on the base, indicated by 38*c*. A rotational bearing 48 can be disposed between the columns and table to allow the table to pivot or rotate, as shown in FIG. 6.

Referring again to FIGS. 1-7, the bath 14 can be cylindrical and transparent, or can have a bath wall 55 that is cylindrical and transparent. The bath 14 can be any desired shape, but cylindrical is believed to be the most efficient because it matches or allows the rotational motion of the arrays 18, 20, and 22 while minimizing volume. The transparent wall 55 allows the breast to be viewed during the scan, and allows a technician to observe operation of the armature 24. Alternatively, the bath wall 55 can be opaque or translucent, and can have a window formed therein. The bath 14 can include one or more holes therein forming inlet and/or outlet openings to allow fluid to enter and/or exit the bath. An upper end of the bath 14 can be open to receive the breast, as described in greater detail below.

The table 38 can be lowered, and the arrays 18, 20 and 22 can be raised or positioned, by the technician visually observing the bath 14, arrays 18, 20 and 22, table 38, and breast, and controlling the table and/or arrays with a manual control 190 (FIG. 1). The manual control 190 can be operatively coupled to the armature 24 to manually move the armature and thus the arrays 18, 20, and 22 within the bath 14. The manual control 190 allows the technician to move about and around the bath 14 as necessary. The manual control 190 can be wired to the system, as shown, or can be a wireless remote control. In one aspect, the manual control 190 can control at least one motor 53 coupled to the armature and a joystick 191 (FIG. 1) operatively coupled to the motor.

Alternatively, the table 38 can be lowered, and the arrays 18, 20 and 22 can be raised or positioned, by the technician visually observing a computer terminal and display 194 (FIG. 1) operatively coupled to a camera (not shown). The computer terminal 194 can include an electronic processor such as is commonly found in a computer workstation, a personal computer, or the like. The computer terminal 194 can include hardware and software that can process data from the transmitter array 18, the receiver array 20, and the reflection array 22 in order to produce a three dimensional graphical representation of the patients breast tissues. The computer terminal 194 is one means for combining data from the transducer arrays into an image of the breast of the patient. Additionally, the manual control 190 and the computer terminal 194 are examples of user interfaces that can be used to control the breast scanning system 10.

The opposing transducer arrays 18 and 20 can be disposed in the bath 14, and carried by an armature 24, also disposed in the bath 14. The armature 24 can include a U-shaped member 124 or yoke disposed on a vertical column 126 that extends through a bottom 16 of the bath 14. The U-shaped member 124 can include a pair of vertical arms 25. Each vertical arm 25 of the U-shaped member can carry one of the opposing arrays 18 and 20. The U-shaped member 124 can be sized to position the arrays 18 and 20 around the breast. As noted above, the opposing arrays 18 and 20 can be a transmitter array 18 and a receiver array 20. Specifically, one of the arrays can be a transmitter array 18 disposed in the bath 14 to transmit ultrasound signals. The other opposing array can be a receiver array 20 disposed in the bath 14 to receive the ultrasound signals from the transmitter array 18.

The armature 24 can also have a third vertical arm 27 that can position the transverse reflection array 22 laterally between the two opposing arrays 18 and 20. The reflection array 22 can be oriented to transmit an acoustic signal substantially perpendicular to the acoustic signals from the transmitter array 18 and received by the receiver array 20. A motor (not shown) can be coupled to the third vertical arm 27 and the transverse reflection array 22 to displace the transverse reflection array independent of the two opposing arrays 18 and 20. In this way the transverse reflection array 22 can be positioned and/or oriented to a location corresponding to an area of interest of the breast either before or after an automatic scanning sequence.

Figure 8:
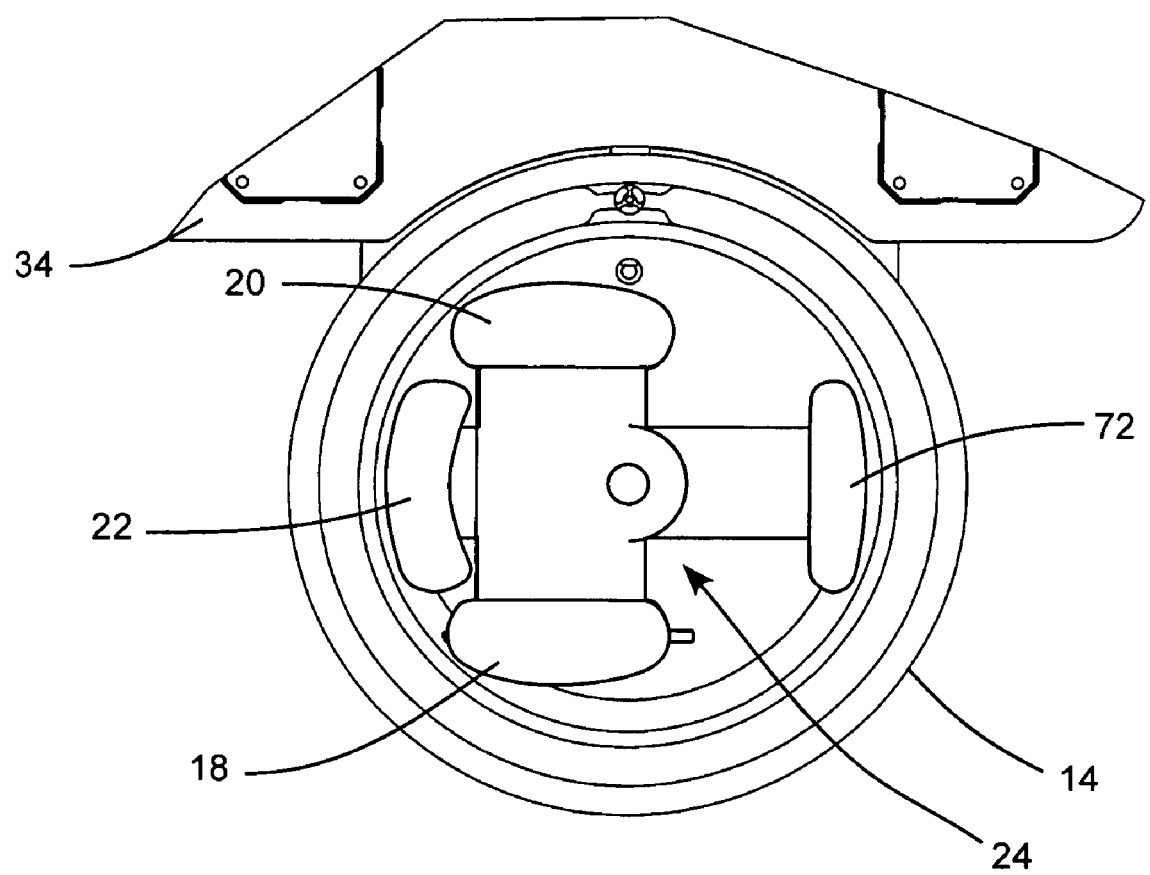
FIG. 8 is a top view of the bath of FIG. 5, shown with an acoustic absorber disposed opposite the reflection array.

In one aspect, the reflection array 22 can be positioned opposite an acoustic absorber 72, as shown in FIG. 8. The acoustic absorber 72 can absorb acoustic signals from the reflection array 22 to minimize undesirable reflection feedback from acoustic signals that were not reflected by the breast tissue. The acoustic absorber 72 can be coupled to the armature 24 and can rotate with the armature so as to remain in a location opposite the reflection array 22.

Figure 9A:
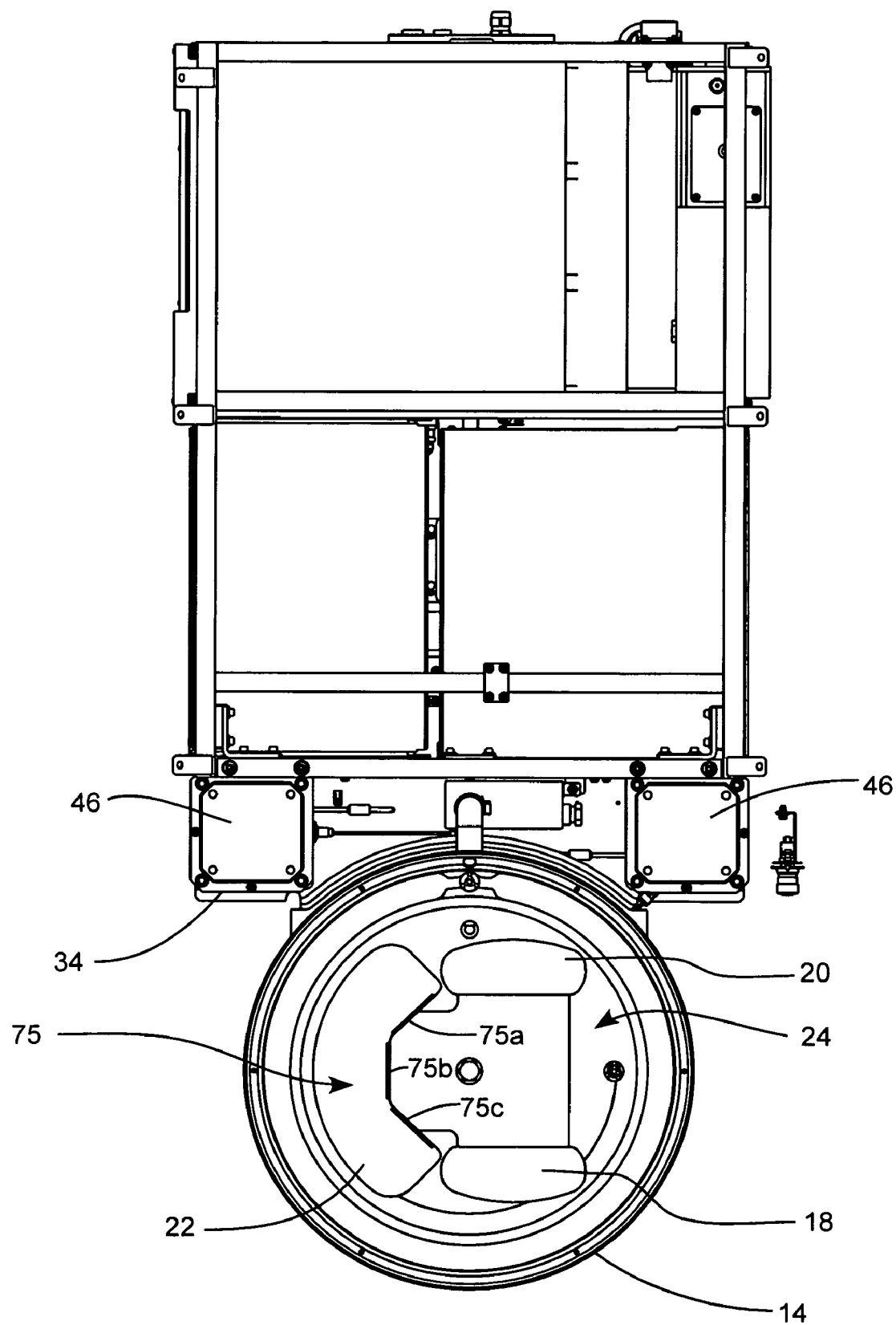
FIG. 9a is a top view of the bath of FIG. 5, shown with three sub-reflection arrays.
Figure 9B:
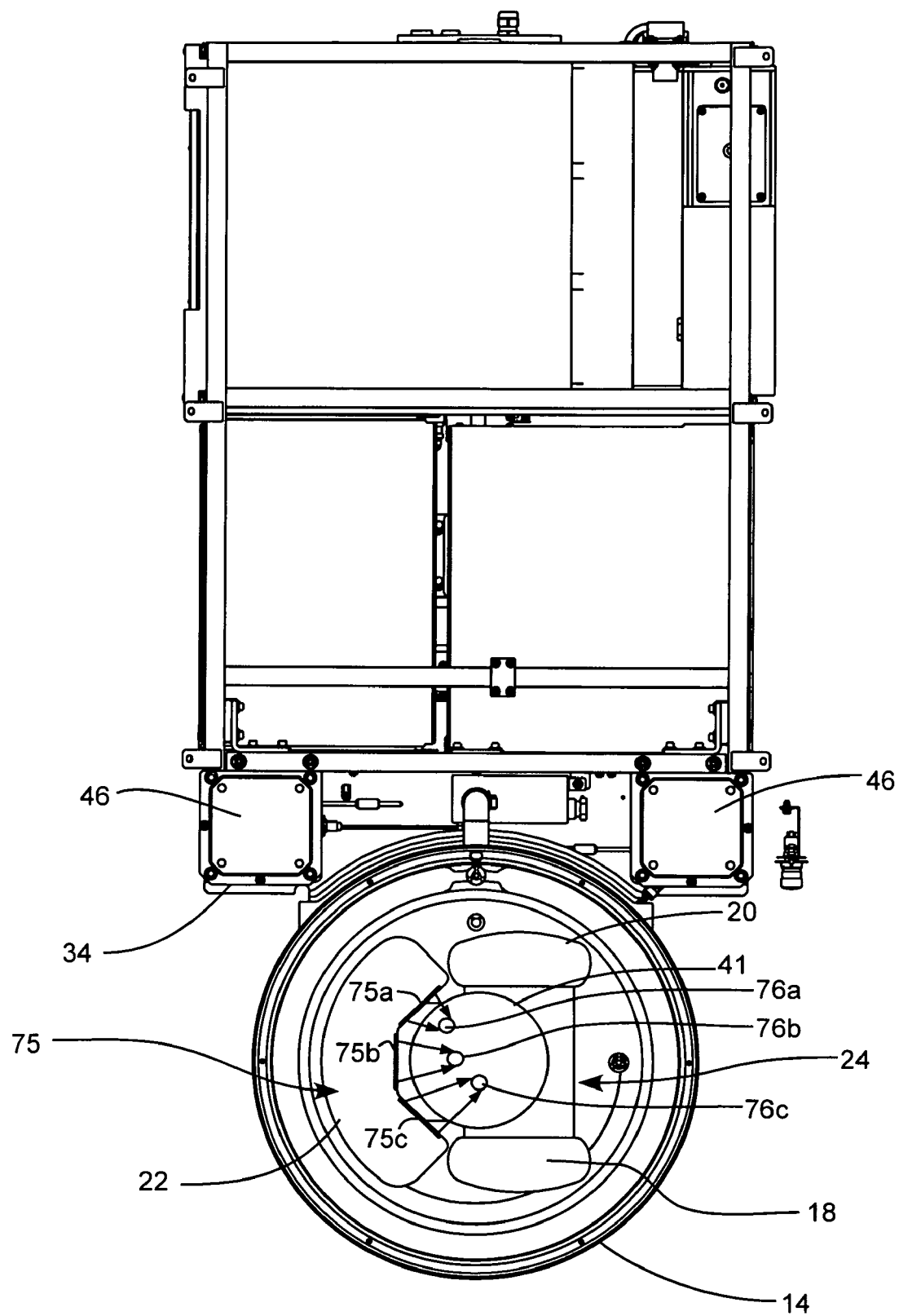
FIG. 9b is a top view of the bath of FIG. 9, shown with each of the three sub-reflection arrays focusing an acoustic signal at a different portion of a breast.

In another aspect, the reflection array 22 can include a plurality of sub-reflection arrays, indicated generally at 75, as shown in FIG. 9. For example, the reflection array 22 can include two or more sub-reflection arrays 75*a*, 75*b*, and 75*c*, as shown in FIGS. 9*a*-9*b*. Each sub reflection array 75*a*, 75*b*, and 75*c* can provide a different beam shape and focal point 76*a*, 76*b*, and 76*c*, respectively, to the acoustic signal transmitted from the reflection array 22 so as to focus the acoustic signal and/or reflection on a particular desired portion of the patient's breast 41, as shown in FIG. 9*b*. In this way, additional high resolution data regarding the patient's breast can be gathered, thereby enhancing the image of the breast tissue.

Figure 7:
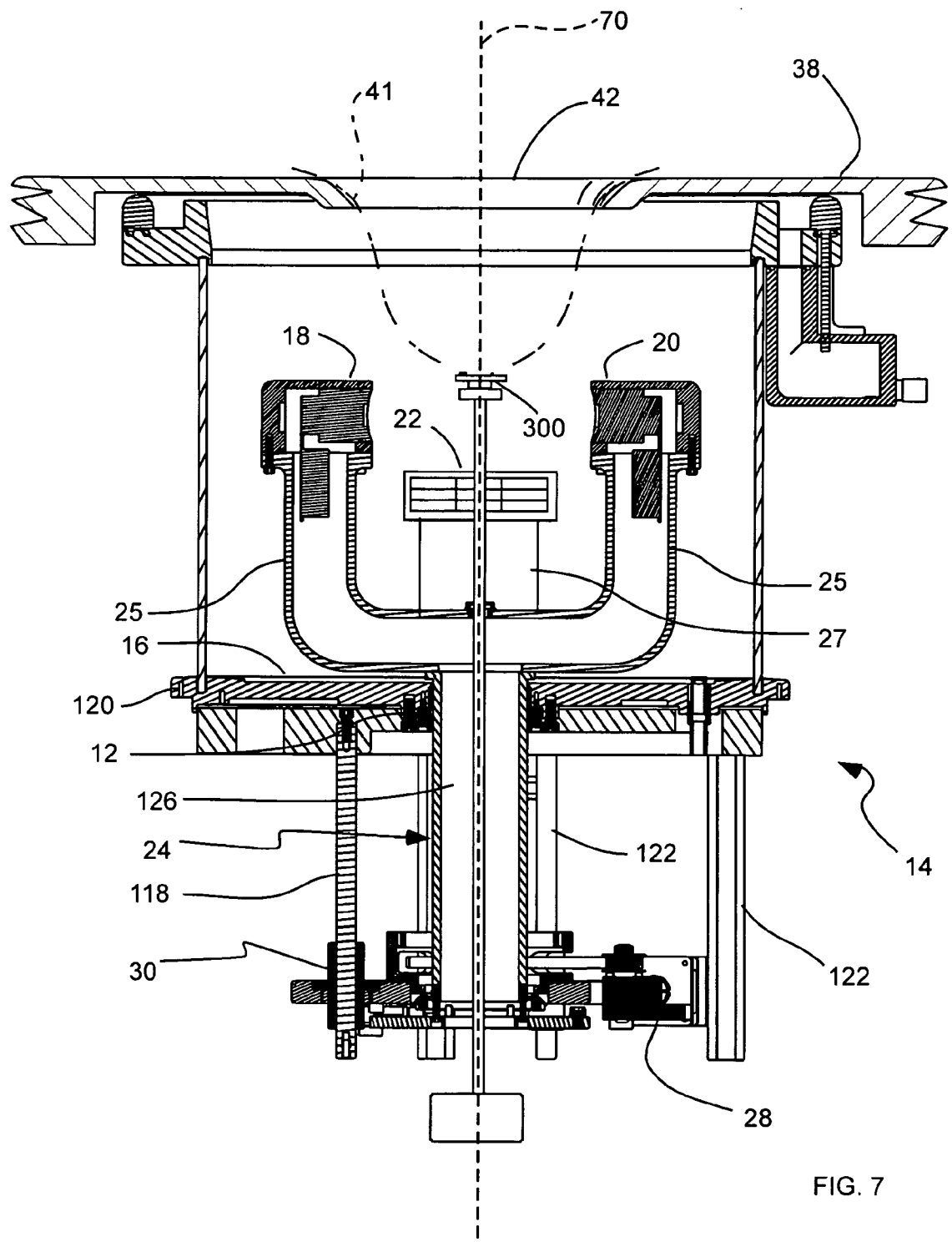
FIG. 7 is a cross-sectional side view of the bath of FIG. 5.

In one aspect, the arrays 18, 20 and 22 can be rotatable around a vertical axis of rotation, indicated by dashed line at 70 in FIG. 7. For example, the vertical column 126 can rotate around in place, thereby rotating the pair of vertical arms 25 and 27 and the arrays 18, 20, and 22. In another aspect (not shown), the transducer arrays 18, 20 and 22 can be off-set, or non-concentric, with respect to an axis of rotation. Similarly, the armature 24 can also be offset or non-concentric with respect to the axis of rotation.

The arrays 18, 20 and 22 can also be displaceable in a vertical direction. A motor 28 can be coupled to the armature 24 to rotate the armature. For example, the motor 28 can be a rotational step motor coupled to the armature 24 or vertical column 126 by a belt (not shown). The motor 28 can turn the belt which can rotate the vertical column and armature.

In addition, a linear motor 30 can be coupled to the armature 24 to linearly displace the armature, and thus the transducer arrays 18, 20, and 22. For example, the vertical column 126 can be carried by a platform 120 supported by a plurality of rods 122. One of the rods 118 can be threaded. The linear motor 30 can engage the threaded rod 118 such that the motor 30 can raise and lower the platform 120, and thus the vertical column 126 along with the rotational motor 28.

A rotational and/or sliding seal 12 can be formed between the bath 14 and the armature 24, or vertical column 126, to seal the bath 14 where the armature 24 or vertical column 126 passes through the bottom 16 of the bath 14. In addition, one or more bearings assemblies (not shown), such as rotational bearings, bearing rings, wheel bearings, and the like, can be disposed between the rotating parts of the vertical column 126 and the stationary parts of the platform 120 to facilitate rotation and reduce frictional forces. Thus, the platform 120 can carry the armature 24 and related motors to move the armature 24 and thus the arrays 18, 20, and 22.

Referring to FIGS. 3 and 4, the breast scanning system can also include a jet 300 disposed in the bath 14 to direct a stream at the breast. The jet 300 can be fixed in the bath or disposed on the armature 24 and rotatable about the breast. In this way, bubbles can be washed from the breast so as to facilitate wetting of the breast by the medium. Similarly, the medium can include a surfactant, as known in the art, to facilitate wetting of the breast and to reduce adherence of bubbles to the breast. It will be appreciated that bubbles on the breast can distort the image generate by the imaging system 10. Thus, advantageously, the jet 300 and surfactant can reduce bubble retention or adhesion on the breast to reduce distortion of the image.

Figure 10:
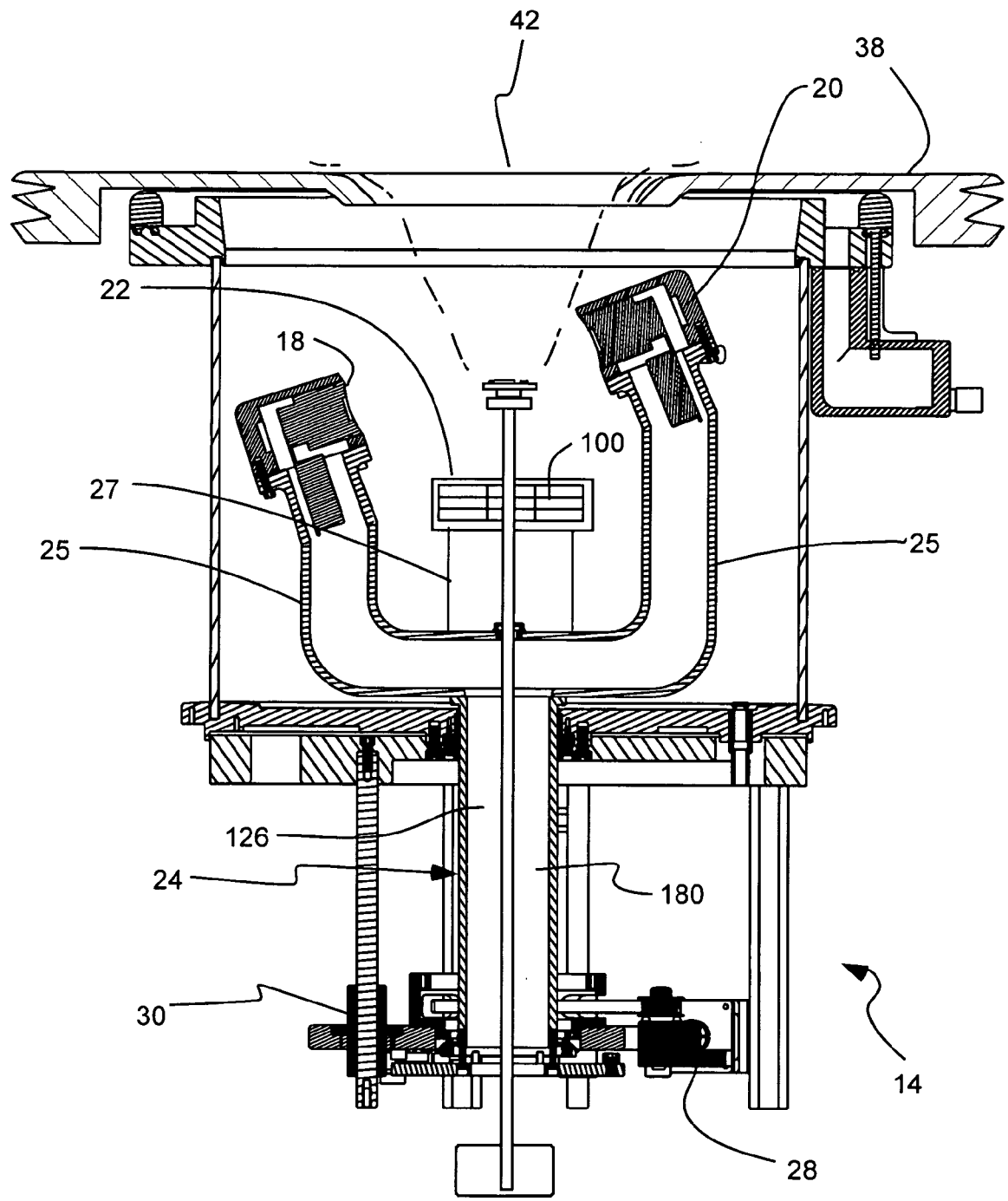
FIG. 10 is a cross-sectional side view of the bath of FIG. 5, shown with transducer arrays at inclined orientations and at differing elevations with respect to one another.

Turning to FIG. 10, in yet another aspect, the transmitter array 18 and the receiver array 20 can be independently moveable with respect to one another. For example, the transmitter 18 and/or receiver 20 can be independently vertically displaceable, such as by a separate linear motor (not shown) coupled between each of the arrays 18 and 20 and the armature 24 or yoke. In this way, additional data can be captured by vertically moving each array 18 and 20 to a desired scanning location without the need for additional elements on the arrays.

In addition, the transmitter array 18 and/or receiver array 20 can be tiltable about a horizontal axis, as shown in FIG. 10. In one aspect, the transmitter array 18 and/or receiver array 20 can be tiltable about a common horizontal axis (or separate horizontal axes). In another aspect, the transmitter array 18 and/or receiver array 20 can tilt independent from one another. The tilt angle can be variable or fixed. Furthermore, the transmitter 18 and/or receiver 20 can be pivotable about a vertical axis. Advantageously, the moveable transducer arrays allow for additional data points from acoustic signals moving through the breast at different angles, and thus results in better imaging of the breast. In addition, greater resolution can be obtained without increasing the number of elements or size of the transducers. Furthermore, such a tiltable configuration can allow imaging closer to the chest wall. Thus, the arrays 18, 20 and 22 can be tilted, or rotatable to have tilted orientation to allow imaging closer to the chest wall.

Additionally, the arrays 18, 20 and 22 can be angled or directed in an upwardly angled direction so that the arrays emit upwardly at an angle and receive downwardly at an angle. The transducer elements 100 can be configured or arrayed differently to have different movement, or even no movement. For example, transducer elements 100 can be vertically oriented along the length of the breast, and can be rotated around the breast, without the need to move the transducers vertically. Alternatively, transducer elements 100 can be horizontally oriented around the circumference of the breast, and can be moved vertically along the length of the breast, without the need to rotate the transducers. Furthermore, the transducer elements 100 can be disposed around the breast, and along the length of the breast, so that the transducers do not have to be moved or rotated.

In use, the linear motor 30 can move (raise or lower) the transducer arrays 18, 20 and 22 sequentially through a plurality of different elevational locations along the breast. The rotational motor 28 can sequentially move (or rotate) the transducer arrays 18, 20 and 22 through a plurality of different angular orientations around the breast at each elevational location. As described above, the arrays 18, 20 and 22 can emit an acoustic pulse at 20 positions (every 18 degrees) around the breast. During the same rotation sequence, the transmitter array 18 can emit an acoustic signal, such as an ultrasound signal, into and through the breast at 180 different locations (every 2 degrees) around the entire breast. The resulting waveforms are received by the opposing receiver array 20. The transmitter array 18 and receiver array 20 can then be moved to a different location along the breast and the sequence can be repeated. In another aspect, the arrays 18 and 20 can emit a continuous acoustic signal during motion. Thus, the movement of the arrays and armature can be discrete, or stepwise through discrete position, or continuous along the entire breast.

Figure 11:
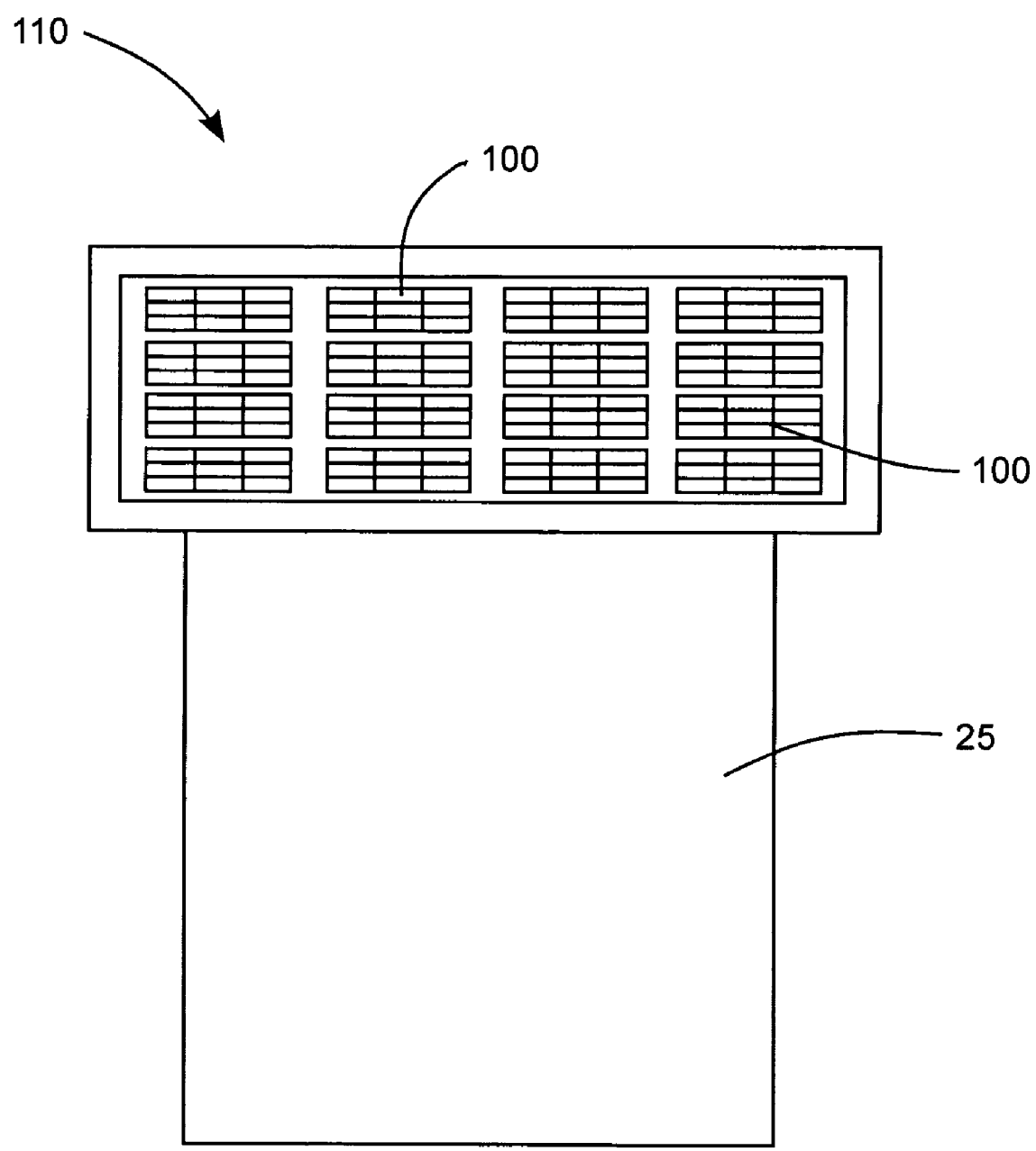
FIG. 11 is a front view of a transducer array on an armature of the breast scanning system of FIG. 1.

Turning to FIG. 11, the transmitter array 18, receiver array 20 and reflection array 22 can have a plurality of acoustic emitters or transducer elements 100 spaced in rows and columns to form an array of transducers, indicated generally at 110. As described above, the transducer arrays 18, 20 and 22 can send and receive acoustic signals at a plurality of elevational locations along the breast, and at a plurality of rotational orientations around the breast at each elevational location.

Figure 12A:
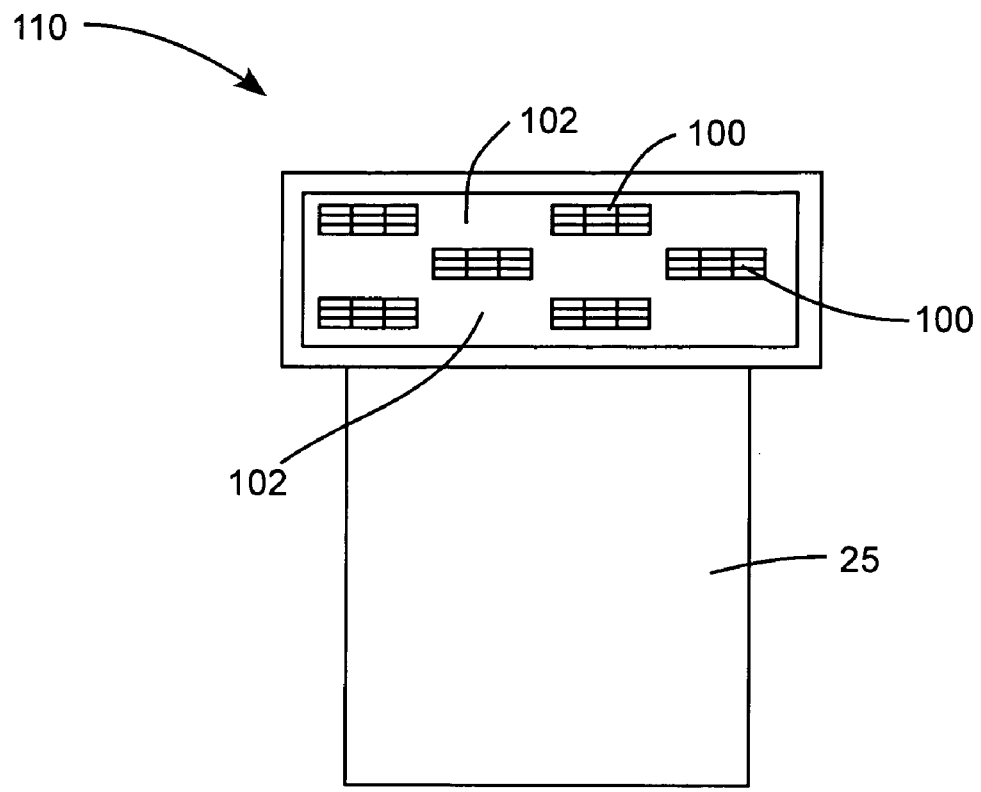
FIG. 12a is a front view of a transducer array on an armature of the breast scanning system of FIG. 1, shown with spacing between acoustic emitters.
Figure 12B:
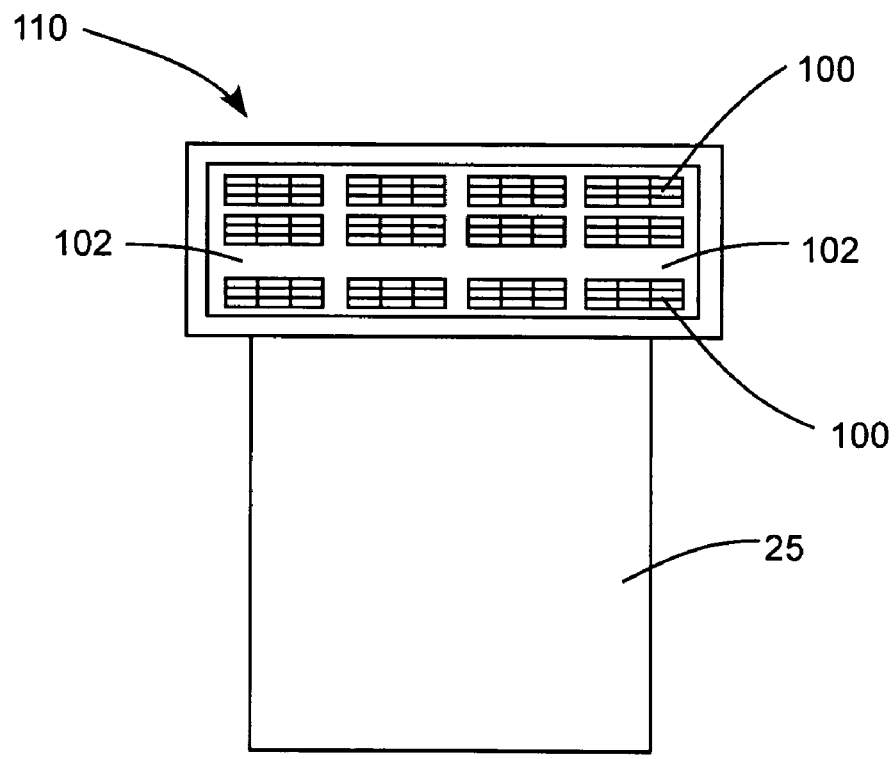
FIG. 12b is a front view of a transducer array on an armature of the breast scanning system of FIG. 1, shown with a distributed spacing of acoustic emitters.

Referring to FIGS. 12a-12b, in one embodiment, the transducer arrays, indicated generally at 110, can have a sparse array of transducer elements 100 that do not fully populate the array leaving greater spacing between the elements. In one aspect, the transducer arrays 18, 20 and 22 can have a random or pseudo-random arrangement of transducer elements 100 that leaves variably sized gaps or spaces 102 between the transducer elements 100, as shown in FIG. 12a. In another aspect, the transducer arrays 18, 20 and 22 can have a greater number of transducer elements 100 at a higher elevational location and a lesser number of elements at a lower elevational location, as illustrated in FIG. 12b. Thus, the transducer elements or emitters 100 can be distributed unevenly across the array 18, 20 and 22. It will be appreciated that in such sparsely populated arrays, the processor 194 (FIG. 1) of the breast scanning system 10 can interpret signals from the arrays based on the pseudo-random arrangement of the sparse array. The processor 194 (FIG. 1) is one means for interpreting the signals from the arrays 18, 20 and 22.

Figure 13:
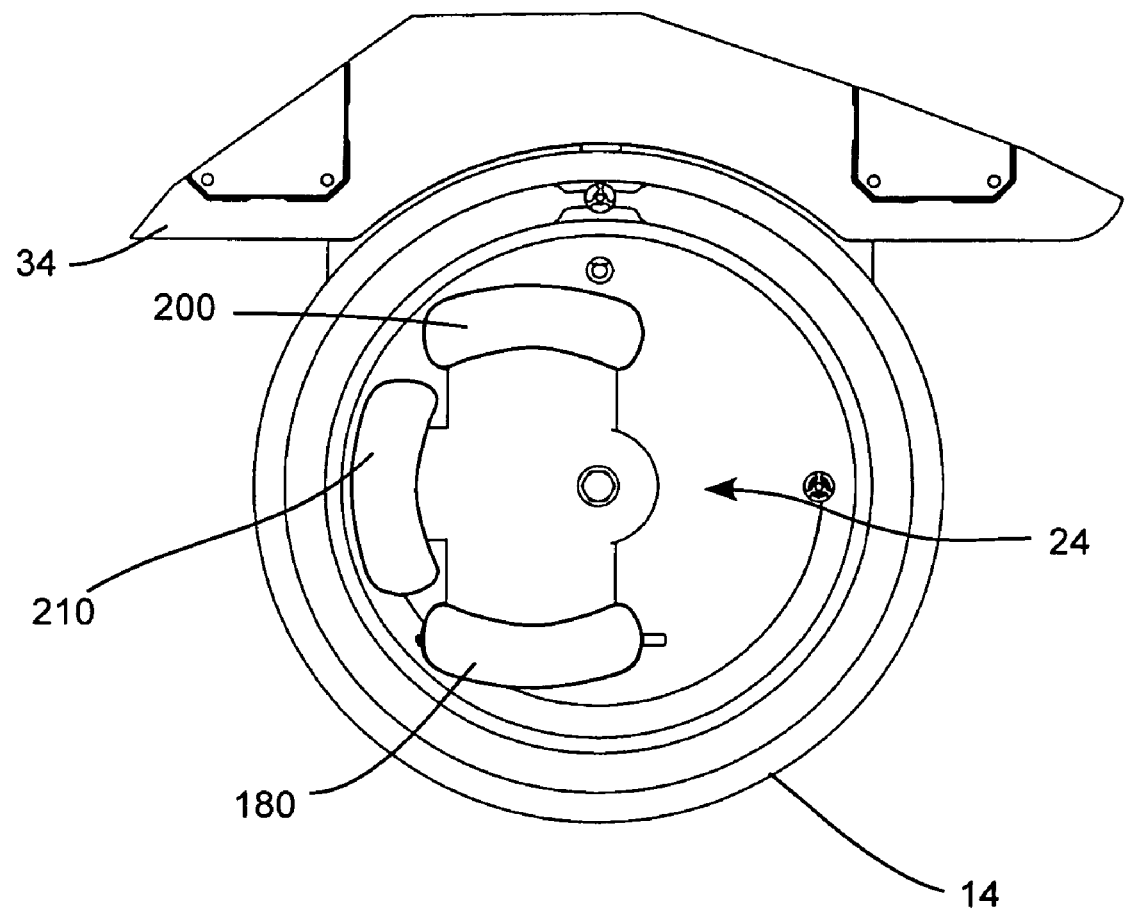
FIG. 13 is a top view of the bath of FIG. 5, shown with concave arcuate transducer arrays.
Figure 14:
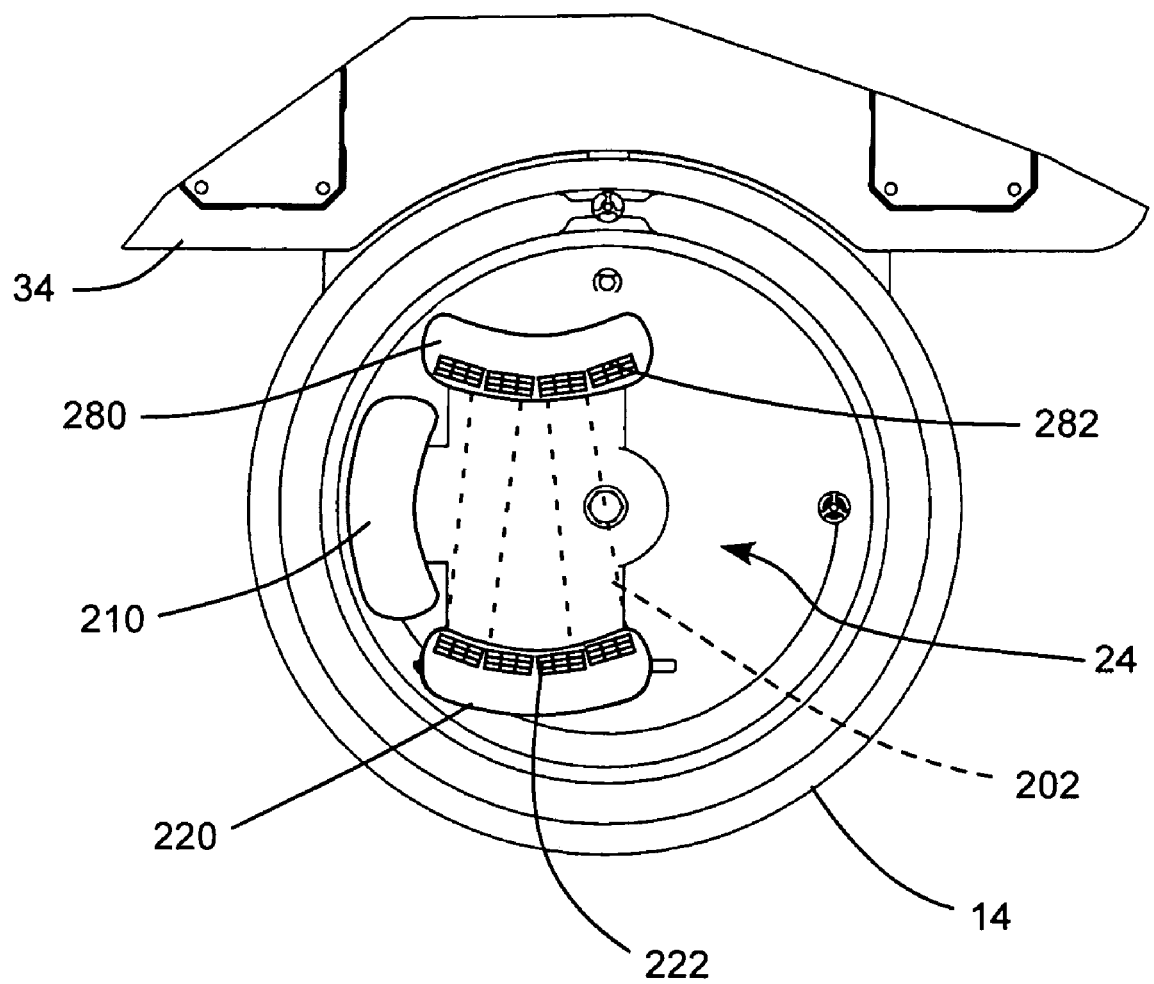
FIG. 14 is a top view of the bath of FIG. 5, shown with concave arcuate transducer arrays forming a divergent acoustic signal beam.

It will be appreciated that, in addition to the generally rectangular arrays shown in FIGS. 1-10, other sized and shaped arrays can also be used, as shown in FIGS. 13-15f. For example, as shown in FIGS. 13-14, the transmitter array 18, receiver array 20, or both arrays can be arcuate in shape, as described below, in order to shape the arrays to approximate the shape of the breast and to minimize transmission of acoustic waves through empty space surrounding the breast. Similarly, as shown in FIGS. 15a-15f, the transmitter array 18, receiver array 20, or both arrays can have non quadrangular or non rectangular shapes so as to reduce elements from the array that would transmit and receive acoustic waves through empty space surrounding the breast. Additionally, the transducer arrays 18, 20 and 22 can also be sized and shaped to scan as the breast as close to the chest wall as possible so as to detect possible tumors or lesions in this difficult to detect region.

Thus, in one aspect, as shown in FIG. 13, the system can include an arcuate receiver array 200 disposable in the bath to receive acoustic signals from the transmitter array 180. The arcuate receiver array 200 can include a curvature within the same plane as the transmitter array 180. In another aspect, the system can include a concave arcuate transmitter 180 array disposable in the bath to transmit ultrasound signals to the receiver array 200. The arcuate transmitter array 180 can include a curvature within the same plane as the receiver array 200. The system can also have an arcuate transverse reflection array 210.

In yet another aspect, as shown in FIG. 14, the transmitter array 220 can be convex and/or can include a plurality of horizontal emitters 222 oriented at divergent angles with respect to one another. Additionally, the receiver array 280 can include a concave curvature within the same plane as the transmitter array. The receiver array can include a plurality of horizontal elements 282. In this way, the transmitter array 220 can include one or more transducer elements or emitters 222 oriented and shaped to produce a divergent beam, shown by dashed line 202.

Figure 15A:
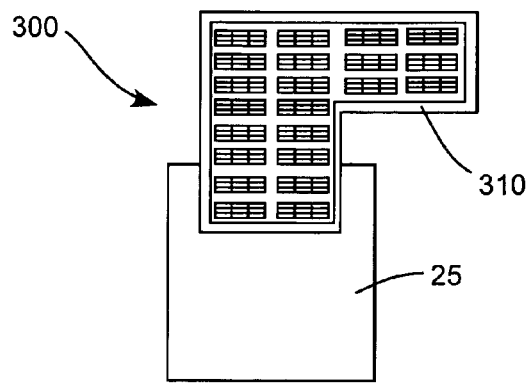
FIGS. 15a-15f illustrate transducer arrays with non rectangular shapes coupled to an armature of the breast scanning system of FIG. 1.
Figure 15B:
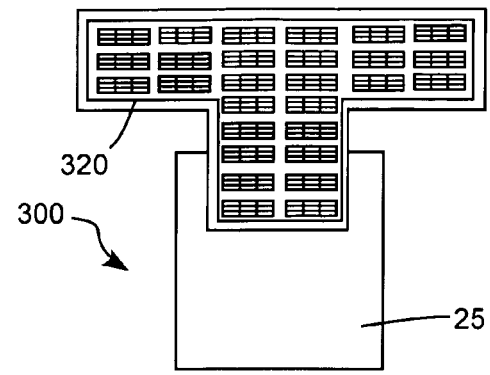
Figure 15C:
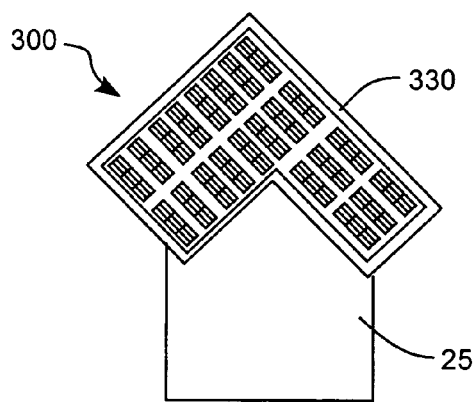
Figure 15D:
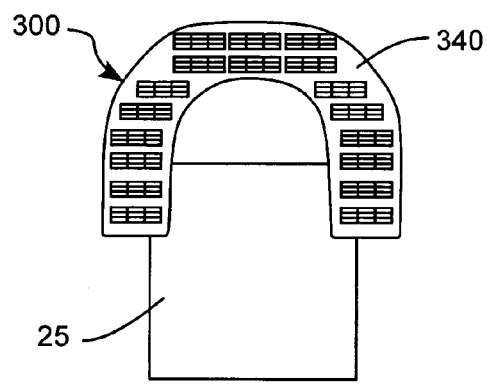
Figure 15E:
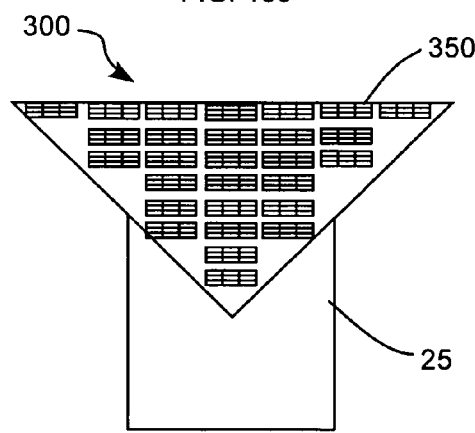
Figure 15F:
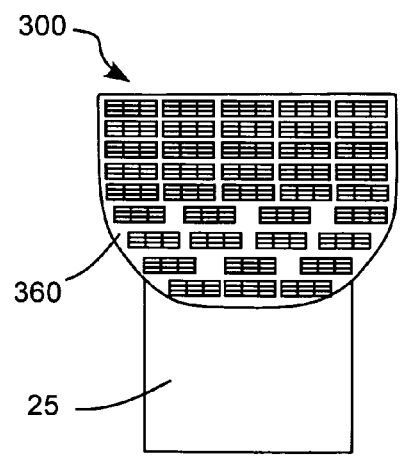

In yet another aspect, at least one of the transducer arrays, indicated generally at 300, can have non-rectangular configurations, as shown in FIGS. 15a-15f. For example, the transmitter array, the receiver array, and/or the reflection array can be an inverted L shaped array 310 as shown in FIG. 15a, a T-shaped array 320 as shown in FIG. 15b, a V-shaped 330 array as shown in FIG. 15c, a U-shaped array 340 as shown in FIG. 15d, a filled V-shaped array 350 as shown in FIG. 15e, or a filled U-shaped array 360 as shown in FIG. 15f. The transducer arrays can also include combinations of the various arrays shown in FIGS. 15a-15f.

Additionally, although not shown in the figures, the non-rectangular configuration of the at least one transducer array can be an inverted L-shaped array, a T-shaped array, a sideways T-shaped array, an inverted V-shaped array, a sideways V-shaped array, an X-shaped array, a U-shaped array, an inverted U-shaped array, a sideways U-shaped array, an H-shaped array, a sideways H-shaped array, a circular O-shaped array, a block O-shaped array, an I-shaped array, a sideways I-shaped array, a filled U-shaped array, or a filled V-shaped array. The transducer array can also include combinations of the various arrays described above.

Figure 16:
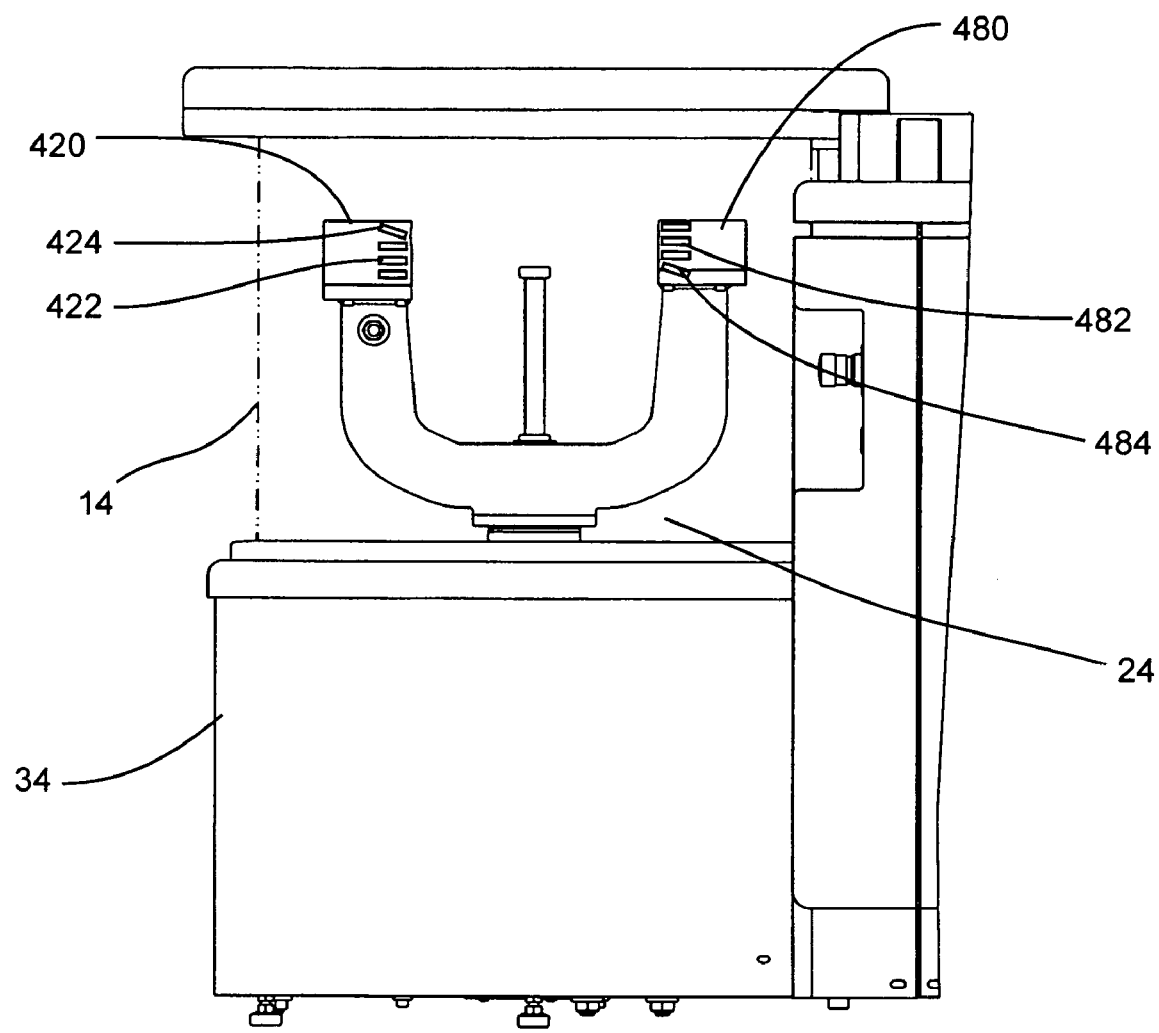
FIG. 16 is a cross sectional side view of the bath of FIG. 5, shown with transducers having rows of emitters with top and bottom rows inclined with respect to on another.

Referring to FIG. 16, the elements that form the transducer arrays can also have various configurations to accommodate a variety of scanning directions and sequences. For example, the transmitter array 420 can include a plurality of rows of elements 422. In one aspect, the rows 422 can be oriented convergent to one another to define a transmitter array 420 with a concave curvature. Additionally, the receiver array 480 can be an arcuate receiver array including a concave curvature with respect to a vertical orientation. The curvature of the receiver array 480 can correspond to the curvature of the transmitter array 420. In this way, at least one of the rows 424 in the transmitter array 420 can be oriented downwardly at an incline and the concave curvature of the receiver array can receive and/or reflect the acoustic wave from the downwardly inclined row 424 of the transmitter array 420.

In another aspect, the transmitter array 420 can have a plurality of rows of elements 422 including an uppermost row 424 facing downwardly at an incline. Additionally, the receiver array 480 can include a plurality of rows of elements 482 including a lowermost row facing upwardly 484 at an incline opposing the uppermost row of the transmitter array. The lowermost row 484 of the receiver array 480 can receive and/or reflect the acoustic wave from the downwardly inclined uppermost row 424 of the transmitter array 420. In this way, the imaging device 10 can scan the breast in an inclined orientation with the acoustic wave transmitting through the breast between locations near the chest wall on one side of the breast to a location near the nipple on an opposite side of the breast. Additionally, other rows 422 and 482 in both the transmitter and the receiver can scan the breast in an orientation relatively parallel to the chest wall. Thus, the imaging device 410 can scan in multiple directions when necessary or desired.

Notwithstanding the forgoing geometrical descriptions of acoustic or ultrasound energy propagating from rows that face each other, such as row 424 facing row 484 and rows 422 facing rows 482, it is clear from scattering theory (P. M. Morse and K. U. Ungard, Theoretical Acoustics, Princeton University Press, Princeton, N.J., Page 413) that information about the distribution of acoustic parameters can be collected from energy that is propagated by scattering events from any transmitting row to any receiving row. Indeed, a greater scattering angle between the normal to the face of the transmitter row and the normal to the face of the receiving array provides the information that creates the greatest vertical spatial resolution. This process is unique to the wave nature of inverse scattering and can not be explained by a purely geometric model that uses the concept of energy traveling from a transducer element on a transmitting row along a straight line to a transducer element on a receiving row.

Referring to FIGS. 17-19, the transducer arrays, indicated generally at 700 can be horizontally and vertically pivotal so as to be able to scan the breast from a variety of inclinations or angles with respect to the chest wall of the patient. For example, in one aspect, an array 700 can be pivotal about a vertical axis to pivot with respect to the opposite array, as shown by dashed lines 702 in FIG. 17. In another aspect, the array 700 can be tiltable about a horizontal axis to tilt with respect to the opposite array, as shown by dashed lines 704 in FIG. 18. In another aspect, an array 700 can be pivotal about a horizontal axis to pivot with respect to the opposite array, as shown by dashed lines 706 in FIG. 19. Thus, as can be seen the arrays can have a wide variety of movement in the vertical direction, the horizontal direction, and in tilting or rotating with respect to one another. In this way, the transmitter array and receiver array can be disposed opposing one another and can be pivotal about a pivot axis to direct the ultrasound signals at an incline through the breast, as shown in FIG. 10.

It will be appreciated that since the arrays can be pivoted about a horizontal and/or vertical axis and that the arrays can also be rotatable about a horizontal and/or vertical axis, then the arrays can be electronically steerable with respect to one another using motors, scales, and positioning hardware, such as screw gears, about a pivot axis. Thus, the transmitter array can be electronically steerable about a pivot axis to pivot with respect to the receiver array. Similarly, the receiver array can be electronically steerable about a pivot axis to pivot with respect to the transmitter array. Additionally, the transverse array can be electronically steerable about a pivot axis to pivot with respect to the transmitter and receiver arrays.

The receiver array can also be electronically steerable with delays so as to emit acoustic pulses sequentially laterally and/or vertically across the array. Similarly, the transmitter can be electronically steerable with delays so as to emit acoustic pulses sequentially laterally and/or vertically across the array. In this way, the transmitter array can be laterally variable across the transmitter array to provide less energy in the ultrasound signal at a perimeter. It will be appreciated that the interface between the breast and the medium, and regions in the bath not containing the patient's breast can cause undesirable noise (in the form of spurious echoes) in the acoustic wave or pulse propagated from the transmitting transducer to the receiving transducer arrays. Thus, the elements in the arrays can vary the energy and/or intensity of the ultrasound signal from emitters corresponding to the breast-medium interface, or along a perimeter of the array. In this way, the array can reduce distortion or noise effects in the data from the imaging system.

Figure 20:
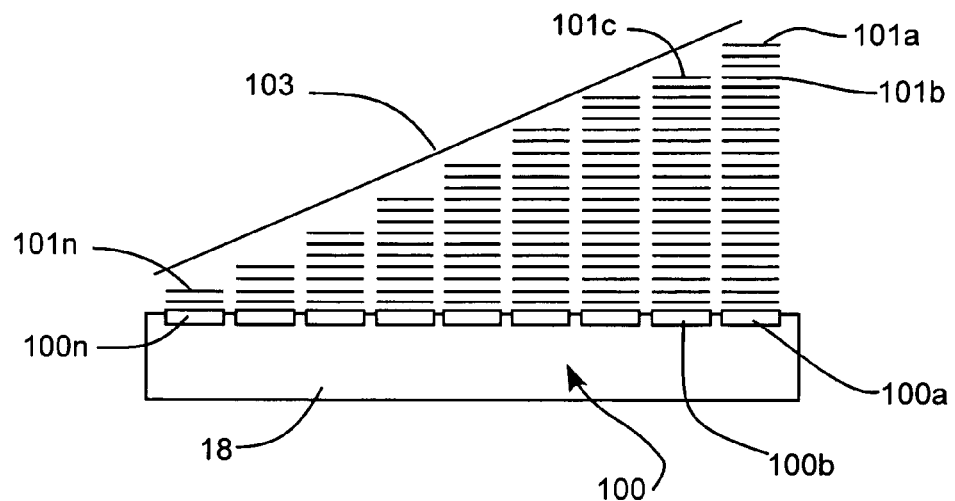
FIG. 20 is a schematic top view of a transducer array shown emitting acoustic pulses in a predetermined pattern.
Figure 21:
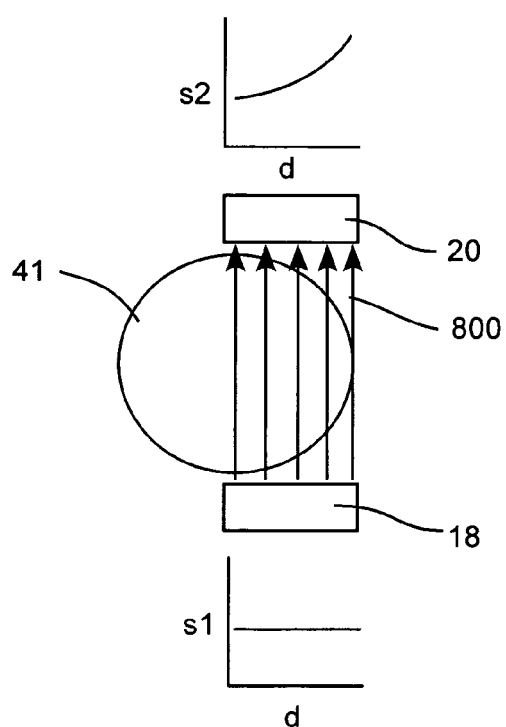
FIG. 21 is a schematic top view of opposing transducer arrays shown emitting acoustic pulses through a breast in a predetermined pattern.

Referring to FIGS. 20-21, the strength and pattern of the acoustic signals transmitted from the transmitter array 18 and/or the reflection array 22 can be varied according to breast tissue and breast geometry variation. For example, acoustic and/or ultrasound pulses can be emitted from transducer emitters 100 in the transmitter array 18 in predetermined patterns of pulses so as to create an acoustic wave front that can correspond to the tissue and geometry of the breast. Thus, as shown in FIG. 20, the emitters 100 in the transducer array 18 can sequentially emit an acoustic pulse starting with a single first pulse 101a from a single emitter 100a followed by a second pulse 101b from the first emitter 100a and a first pulse 101c from a second sequential emitter 100b. The sequential pattern can be repeated and an additional emitter 100n can be added with each acoustic pulse 101n until all of the emitters in the array emit an acoustic pulse. In this way, the transmitter array can generate an angled wave front 103.

It will be appreciated that the transmitter array 18 can generate other shaped wave fronts by varying the emitter pulse pattern and sequence. In this way, the transmitter array 18 can produce a predetermined wave front that can correspond the tissue and geometry of a breast, and in particular to the breast being examined by the breast scanning system 10.

Figure 22:
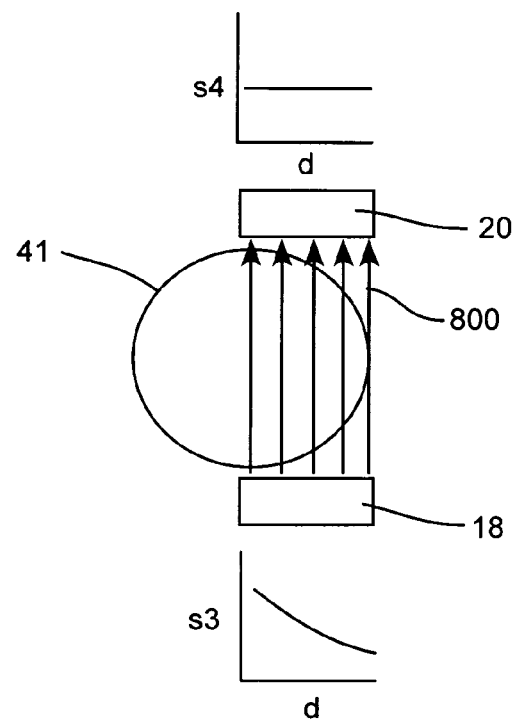
FIG. 22 is a schematic top view of opposing transducer arrays shown emitting acoustic pulses through a breast in a predetermined pattern.

Additionally, the strength of the acoustic signal can be varied across the transmitter array 18 and/or reflection array 22, as shown in FIGS. 21-22. It will be appreciated that the density of breast tissue can vary across the breast and that the amount of breast tissue through which the signal passes can vary based on the geometry of the breast. Accordingly, as shown in FIG. 21, an acoustic signal, indicated generally at 800, transmitted from the transmitter array 18 having a consistent signal strength, indicated generally at s1 in the signal strength plot adjacent the transmitter array 18, across the transmitting region, d, of the transmitter array 18 can result in a variable signal strength, indicated generally at s2 in the plot adjacent the receiver array 20, in the acoustic signal received by the receiver array 20. Advantageously, as shown in FIG. 22, the strength of the acoustic signal, indicated at s3 in the signal strength plot adjacent the transmitter array 18, from the transmitter array 18 can be varied across the transmitting region, d, in the transmitter array 18 in order to compensate for breast tissue and geometry differences. In this way, the acoustic signal, indicated as S4 in the signal strength plot adjacent the receiver array 22 received by the receiver array 22 can have a consistent signal strength.

The present invention also provides for a method for imaging a breast of a patient including disposing the breast into a bath of some acoustic medium that is essentially transparent or of a chosen transmission coefficient to augment breast imaging by nearly matching the acoustic properties of the breast.

The present invention also provides for a method for imaging a breast of a patient including disposing the breast into a bath of medium. The breast can be automatically scanned with ultrasound or acoustic signals from transducer arrays to create a three-dimensional image of the breast and to locate a position of a tumor or a lesion in the breast with respect to the three-dimensional image. The automatic scanning can include automatically sequentially moving transducer arrays through a plurality of different elevational locations along the breast, and sequentially moving the transducer arrays through a plurality of different angular orientations around the breast at each elevational location. At least one transducer array can be moved manually to an elevational location corresponding to an array of interest of the breast either before or after automatically scanning. The at least one transducer array can be moved manually by engaging a joystick operatively coupled to the at least one transducer array.

The present invention also provides for a method for imaging a breast of a patient including disposing the breast into a bath of medium. Ultrasound signals can be transmitted from a transmitter array disposed in the bath. The ultrasound signals can be received with a receiver array disposable in the bath with a sparse vertical array with elements that do not fully populate the vertical array leaving greater spacing. A three-dimensional image of the breast can be created and a position of a tumor or a lesion can be located in the breast with respect to the three-dimensional image based on pseudo-random arrangement of the sparse vertical array.

The present invention also provides for a method for imaging a breast of a patient including disposing the breast into a bath of medium. Ultrasound signals can be transmitted from a transmitter array disposed in the bath. The ultrasound signals can be received with a receiver array disposable in the bath. The receiving array can be subsequently rotated with respect to the transmitter array about a horizontal axis. Additional ultrasound signals can be subsequently received from the transmitter array. A three-dimensional image of the breast can be created and a position of a tumor or a lesion can be located in the breast with respect to the three-dimensional image.

The present invention also provides for a method for imaging a breast of a patient including disposing the breast into a bath of medium. Ultrasound signals can be transmitted from a transmitter array disposed in the bath. The ultrasound signals can be received with a receiver array disposable in the bath with a sparse vertical array. The ultrasound signal from the transmitter array can be varied laterally to reduce an energy of the ultrasound signal at a perimeter. A three-dimensional image of the breast can be created and a position of a tumor or a lesion can be located in the breast with respect to the three-dimensional image.

The present invention also provides for a method for imaging a breast of a patient including disposing the breast into a bath of medium. Ultrasound signals can be transmitted from a transmitter array disposed in the bath. The ultrasound signals can be received with a receiver array disposable in the bath. The transmitting array and the receiving array can subsequently be rotated together about a horizontal axis while maintaining an opposing relationship between the arrays. Additional ultrasound signals can be subsequently received from the transmitter array. A three-dimensional image of the breast can be created and a position of a tumor or a lesion can be located in the breast with respect to the three-dimensional image.

The present invention also provides for a method for imaging a breast of a patient including disposing the breast into a bath of medium. A stream of fluid can be directed at the breast with a jet to remove air bubbles from the breast. Ultrasound signals can be emitted from a transmitter array disposed in the bath. Ultrasound signals can be subsequently received from the transmitter array. A three-dimensional image of the breast can be created and a position of a tumor or a lesion can be located in the breast with respect to the three-dimensional image.

The present invention also provides for a method for imaging a breast of a patient including disposing the breast into a bath of medium. Ultrasound signals can be transmitted from a transmitter array disposed in the bath. An ultrasound image of the breast base can be developed on the ultrasound signals. Ultrasound signals can be emitted from another transmitter array. The ultrasound signals from the another transmitter can be received with a receiver array. A three-dimensional image of the breast can be created and a position of a tumor or a lesion can be located in the breast with respect to the three-dimensional image. The ultrasound image can be compared to the three-dimensional image.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A breast scanning system configured to scan a breast of a patient, comprising:
 a) a transmitter array configured to transmit acoustic signals through the breast;

b) a receiver array positioned to receive acoustic signals from the transmitter array to obtain transmission attenuation data;

c) a reflection array disposed laterally between the transmitter array and the receiver array, and configured to transmit acoustic signals through the breast and receive reflected acoustic signals from the breast to obtain reflection data from the breast;

d) a table configured to receive the patient thereon, having an aperture formed therein configured to receive the breast of the patient pendant therethrough and positionable over and into a bath configured to contain a medium; and e) an armature movably disposable in the bath and configured to carry the arrays.

2. A system in accordance with claim 1, further comprising:
an acoustic absorber disposed opposite the reflection array to absorb acoustic signals from the reflection array.

3. A system in accordance with claim 1, further comprising:
means for combining transmission speed of sound and/or attenuation data from the receiver array and reflection data from the reflection array into an image of the breast of the patient.

4. A system in accordance with claim 1, wherein the reflection array includes at least two sub-reflection arrays and each sub-reflection array is shaped to provide a different beam shape and focal point to the acoustic signal.

5. A system in accordance with claim 1, wherein the transmitter array and the receiver array are arcuate in a horizontal plane and have a curvature within a common plane.

6. A system in accordance with claim 1, wherein the transmitter array and the receiver array are sparse arrays with transducer elements that do not fully populate the arrays leaving greater spacing between the transducer elements.

7. A system in accordance with claim 1, wherein the transmitter array is a convex arcuate transmitter array.

8. A system in accordance with claim 1, wherein the transmitter array includes a plurality of rows oriented convergent to one another to define a transmitter array with a concave curvature.

9. A system in accordance with claim 1, wherein the transmitter array is laterally variable across the transmitter array with respect to strength of an acoustic signal transmitted from the transmitter array to provide relatively less energy in the acoustic signal at a desired area of the transmitter array.

10. A system in accordance with claim 1, wherein at least one of the transmission array and the receiver array has a non-rectangular configuration selected from the group consisting of an L-shaped array, an inverted L-shaped array, a T-shaped array, an inverted T-shaped array, a sideways T-shaped array, a V-shaped array, an inverted V-shaped array, a sideways V-shaped array, an X-shaped array, a U-shaped array, an inverted U-shaped array, a sideways U-shaped array, an H-shaped array, a sideways H-shaped array, a circular O-shaped array, a block O-shaped array, an I-shaped array, a sideways I-shaped array, a filled U-shaped array, a filled V-shaped array, and combinations thereof.

11. A system in accordance with claim 10, wherein the at least one array includes a greater number of transducer elements at a higher elevational location and a lesser number of transducer elements at a lower elevational location.

12. A system in accordance with claim 1, wherein the transmitter array and the receiver array are disposed opposing one another and are pivotal about a horizontal pivot axis to direct the acoustic signals at an incline with respect to the breast of the patient.

13. A system in accordance with claim 12, wherein the transmitter array includes a plurality of rows of elements with an uppermost row facing downwardly at an incline, and the receiver array includes a plurality of rows of elements with a lowermost row facing upwardly at an incline opposing the uppermost row of the transmitter array.

14. A system in accordance with claim 1, wherein the transmitter array and the receiver array are rotatable with respect to each other about a vertical axis.

15. A system in accordance with claim 1, wherein the transmitter array is electronically steerable about a pivot axis to pivot with respect to the receiver array, and the receiver array is electronically steerable about a pivot axis to pivot with respect to the receiver array.

16. A system in accordance with claim 15, wherein arrays are steerable with delays so as to emit acoustic pulses sequentially laterally and vertically across the array.

17. A system in accordance with claim 1, further comprising means for extending breast tissue to draw the breast tissue away from a wall of a chest of the patient to allow acoustic signals from the arrays to pass through the extended breast tissue.

18. A system in accordance with claim 1, wherein the reflection array is separate and discrete from the transmitter array and the receiver array.

19. A system in accordance with claim 1, wherein the reflection array is carried by an armature.

20. A system in accordance with claim 1, further comprising a yoke with pair of vertical arms carrying the transmitter and receiver arrays, and a third vertical arm carrying the reflection array.

21. A breast scanning system configured to scan a breast of a patient, comprising:
a) a table configured to receive the patient thereon, having an aperture formed therein configured to receive the breast of the patient pendant therethrough and positionable over and into a bath configured to contain a medium;

b) an armature movably disposable in the bath and configured to carry the arrays;

c) transducer arrays disposable in the bath, and including a transmitter array configured to transmit acoustic signals through the breast, and a receiver array configured receive acoustic signals to obtain transmission attenuation data from the breast; and d) a reflection array to transmit acoustic signals through the breast and receive reflected acoustic waves from the breast to obtain reflection data from the breast.

22. A system in accordance with claim 21, further comprising:
a) a friction surface surrounding the aperture and having a relatively higher friction coefficient than the table to resist movement of the breast of the patient out of the aperture.

23. A system in accordance with claim 21, further comprising:
a) a seal disposed between the bath and the table to seal the table to the bath when the table is positioned against the bath;

b) a seal surface surrounding the aperture and positioned to seal against skin of a chest wall of the patient when the patient lies upon the table; and c) a vacuum fluidly coupled to the bath and configured to draw a vacuum pressure on the bath to draw the breast of the patient into the bath.

24. A breast scanning system configured to scan a breast of a patient, comprising:
   a) transducer arrays disposable in a bath, and including a transmitter array configured to transmit acoustic signals through the breast, and a receiver array configured receive acoustic signals to obtain transmission attenuation data from the breast;
   b) a reflection array to transmit acoustic signals through the breast and receive reflected acoustic waves from the breast to obtain reflection data from the breast;
   c) means for combining the transmission attenuation data from the transducer arrays and reflection data from the reflection array into an image of the breast of the patient;
   e) a table configured to receive the patient thereon, having an aperture formed therein configured to receive the breast of the patient pendant therethrough and positionable over and into a bath configured to contain a medium; and
   e) an armature movably disposable in the bath and configured to carry the arrays.

* * * * *